US010792284B2

(12) United States Patent
Lowe et al.

(10) Patent No.: US 10,792,284 B2
(45) Date of Patent: Oct. 6, 2020

(54) SYNERGISTIC CANCER TREATMENT

(71) Applicant: Memorial Sloan Kettering Cancer Center, New York, NY (US)

(72) Inventors: Scott W. Lowe, New York, NY (US); Neal Rosen, New York, NY (US); Eusebio Manchado-Robles, Basel (CH); Susann Weissmueller, Basel (CH)

(73) Assignee: Memorial Sloan Kettering Cancer Center, New York, NY (US)

( * ) Notice: Subject to any disclaimer, the term of this patent is extended or adjusted under 35 U.S.C. 154(b) by 257 days.

(21) Appl. No.: 15/550,432

(22) PCT Filed: Feb. 12, 2016

(86) PCT No.: PCT/US2016/017750
§ 371 (c)(1),
(2) Date: Aug. 11, 2017

(87) PCT Pub. No.: WO2016/130917
PCT Pub. Date: Aug. 18, 2016

(65) Prior Publication Data
US 2018/0036309 A1    Feb. 8, 2018

Related U.S. Application Data

(60) Provisional application No. 62/117,856, filed on Feb. 18, 2015, provisional application No. 62/115,613, filed on Feb. 12, 2015.

(51) Int. Cl.
| | |
|---|---|
| *A61K 31/519* | (2006.01) |
| *A61K 31/506* | (2006.01) |
| *A61K 31/496* | (2006.01) |
| *C07D 487/04* | (2006.01) |
| *C07D 471/04* | (2006.01) |
| *A61K 31/5025* | (2006.01) |
| *A61K 31/713* | (2006.01) |
| *C07K 16/40* | (2006.01) |
| *C12Q 1/6886* | (2018.01) |
| *G01N 33/574* | (2006.01) |

(52) U.S. Cl.
CPC .......... *A61K 31/519* (2013.01); *A61K 31/496* (2013.01); *A61K 31/506* (2013.01); *A61K 31/5025* (2013.01); *A61K 31/713* (2013.01); *C07D 471/04* (2013.01); *C07D 487/04* (2013.01); *C07K 16/40* (2013.01); *C12Q 1/6886* (2013.01); *C12Y 207/10001* (2013.01); *C12Y 207/12002* (2013.01); *G01N 33/57492* (2013.01); *C12Q 2600/106* (2013.01); *C12Q 2600/158* (2013.01); *G01N 2333/71* (2013.01); *G01N 2333/912* (2013.01); *G01N 2440/14* (2013.01)

(58) Field of Classification Search
CPC .............. A61K 31/713; A61K 31/5025; A61K 39/001107; A61K 39/001102; G01N 2440/14; G01N 33/57492; G01N 2333/71; C07K 16/40; C12Y 207/10001; C12Y 207/12002

See application file for complete search history.

(56) References Cited

U.S. PATENT DOCUMENTS

| | | |
|---|---|---|
| 2011/0027275 A1 | 2/2011 | Ferrara et al. |
| 2012/0315648 A1 | 12/2012 | Graus Porta et al. |
| 2013/0217721 A1 | 8/2013 | Lo et al. |

FOREIGN PATENT DOCUMENTS

| | | |
|---|---|---|
| WO | WO-2010/020703 A1 | 2/2010 |
| WO | WO-2010/036917 A1 | 4/2010 |
| WO | WO-2013/019620 | 2/2013 |
| WO | WO-2014/138279 A1 | 9/2014 |
| WO | WO-2014/145751 | 9/2014 |

OTHER PUBLICATIONS

Ebi et al (Journal of Clinical Investigation, 2011, vol. 121, pp. 4311-4321) (Year: 2011).*
Agell et al, Cellular Signaling, 2002, vol. 14, pp. 649-654 (Year: 2002).*
Robinson, PLoS Biology, 2004, vol. 1, pp. 0018-0020 (Year: 2004).*
Tolcher et al (Clinical Cancer Research, 2002, vol. 8, pp. 2530-2535) (Year: 2002).*
James and Gibson (Blood, 1998, vol. 91, pp. 371-382) (Year: 1998).*
Takahashi et al (Clinical Cancer Research, 2012, vol. 18, pp. 1641-1654) (Year: 2012).*
Walters et al (Neoplasia, 2013, vol. 15, pp. 143-155) (Year: 2013).*
NCT01229150 (ClinicalTrial.gov Archive, Oct. 23, 2014) (Year: 2014).*
Lehnen et al (Histopathology, 2013, vol. 63, pp. 157-166) (Year: 2013).*
Bejanyan et al (Cancer, 2012, vol. 118, pp. 3968-3976) (Year: 2012).*
Mirzoeva et al (Cancer Research, 2009, vol. 69, pp. 565-572) (Year: 2009).*
Ong et al (PNAS, 2001, vol. 98, pp. 6074-6079) (Year: 2001).*
Duncan et al (Cell, 2012, vol. 149, pp. 307-321) (Year: 2012).*
Lorenzer et al (Journal of Controlled Release 2015, vol. 203, pp. 1-15) (Year: 2015).*
Merkel et al (Advanced Drug Delivery Reviews, 2014, vol. 75, pp. 112-128) (Year: 2014).*
Rao et al (Advanced Drug Delivery Reviews, 2009, vol. 61, pp. 746-759) (Year: 2009).*
Moore et al ('Short Hairpin RNA (shRNA): Design, Delivery, and Assessment of Gene Knockdown', In: RNA Therapeutics M. Sioud, Ed., Methods in Molecular Biology, 2010, vol. 629, pp. 139-156) (Year: 2010).*

(Continued)

*Primary Examiner* — Karen A. Canella
(74) *Attorney, Agent, or Firm* — Foley & Lardner LLP

(57) ABSTRACT

The use of mitogen activated kinase inhibition therapy in combination with receptor tyrosine kinase therapy for the treatment of cancer is described.

10 Claims, 30 Drawing Sheets

(56) References Cited

OTHER PUBLICATIONS

Amit Dutt et al: "Inhibitor-Sensitive FGFRI Amplification in Human Non-Small Cell Lung Cancer, art. e20351", PLOS One, vol. 6, No. 6, Jun. 7, 2011, pp. 1-10.
International Search Report and Written Opinion, PCT/US2016/17750, Memorial Sloan Kettering Cancer Center, 12 pages (Jul. 26, 2016).
Z. Tao et al: "Coadministration of 1-15Trametinib and Palbociclib Radiosensitizes KRAS-Mutant Non-Small Cell Lung Cancers In Vitro and In Vivo", Clinical Cancer Research, vol. 22, No. I, Jan. 1, 2016, pp. 122-133.
Sun C et al: "Intrinsic resistance to MEK inhibition in KRAS mutant lung and colon cancer through transcriptional induction of ERBB3", Cell Reports,, vol. 7, No. 1, Apr. 10, 2014, pp. 86-93.
Leo Y. Luo et al: "The Tyrosine Kinase Adaptor Protein FRS2 Is Oncogenic and Amplified in High-Grade Serous Ovarian Cancer", Molecular Cancer Research, vol . 13, No. 3, Nov. 3, 2014, pp. 502-509.

\* cited by examiner

A

B

A

B

C

A

C

D

A

B

C

A

B

US 10,792,284 B2

SYNERGISTIC CANCER TREATMENT

CROSS REFERENCE TO RELATED APPLICATIONS

This applications claims priority to U.S. provisional application Ser. No. 62/115,613 filed on Feb. 12, 2015 and Ser. No. 62/117,856 filed on Feb. 18, 2015 each of which is incorporated herein in its entirety by this reference.

GOVERNMENT SUPPORT

This invention was made with government support under CA129243 and CA197504 awarded by the National Institutes of Health. The government has certain rights in the invention.

BACKGROUND

Kinases are implicated in numerous cancers and therefore are an attractive therapeutic target. Resistance to kinase directed therapies can develop. There is a need for new combinatorial therapy, particularly with synergistically acting agents, to improve overall survival.

SUMMARY

The present disclosure provides novel therapies for use, for example in the treatment of cancer. In some embodiments, provided therapies are combination therapies. In some embodiments, the present disclosure provides therapies that are particularly useful in the treatment of KRAS mutant lung cancers. Those skilled in the art will be aware that no efficacious treatment was previously available for such cancers.

Among other things, the present disclosure encompasses the recognition that therapies utilizing MEK inhibitors can lead to increased expression or activity of receptor tyrosine kinases. The present disclosure thus identifies the source of a problem with MEK inhibition therapy. The present disclosure demonstrates that RTK inhibition therapy can provide synergistic benefits when combined with MEK inhibitor therapy. The present disclosure particularly demonstrates that RTK inhibition therapy can delay, avoid, and/or reverse resistance to MEK inhibitor therapy.

The present disclosure identifies and demonstrates the roles of certain markers revealing development of resistance to MEK inhibition therapy, and establishes that detection or characterization of one or more such markers can usefully be utilized in the course of therapy, for example to identify subjects who may be suffering from or susceptible to such resistance and/or may benefit from treatment with RTK inhibition therapy. In some particular embodiments, such markers may usefully be utilized to select a particular RTK inhibition therapy regimen (e.g., with a particular RTK inhibitor and/or according to a particular route of administration and/or dosing schedule). For example, a marker that reveals or represents increased level or activity of one or more particular RTKs may indicate potential effectiveness of RTK inhibition therapy targeting that one or more particular RTK(s).

In certain embodiments, the present disclosure recognizes benefits of combination therapies as described herein notwithstanding literature reports or other teachings that might otherwise lead those skilled in the art to expect combinations as described herein to be ineffective in particular contexts. The present disclosure therefore provides recognition of the source of a problem in such reports or teachings.

BRIEF DESCRIPTION OF THE DRAWING

The following figures are presented for the purpose of illustration only and are not intended to be limiting

DEFINITIONS

Figure 1:
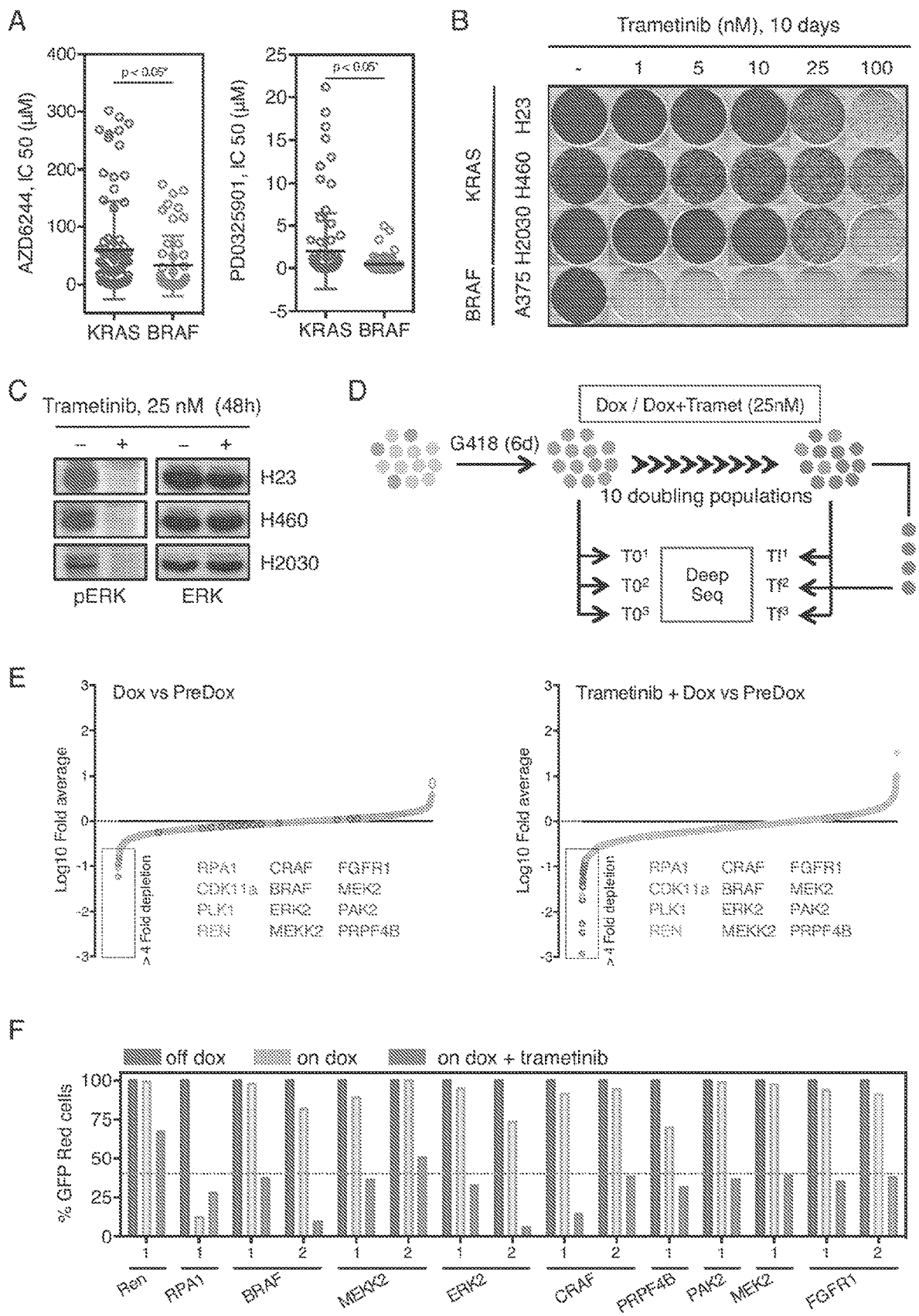
FIG. 1 shows suppression of FGFR1 and MAPK signaling effectors sensitize KRAS-mutant lung tumors to MEK inhibition. a, The Genomic of Drug Sensitivity in Cancer dataset was analyzed to determine if sensitivity to MEK inhibitors AZD6244 and PD0325901 correlates with tumor genotype. The IC50 of AZD6244 and PD0325901 in KRAS- and BRAF-mutant cell lines is shown. *$p<0.05$. b, Clonogenic assay of KRAS-(H23, H460, H2030) and BRAF-mutant lung cancer cell lines. Cells were cultured in the absence or presence of trametinib at the indicated concentrations for 8-10 days. Remaining cells were fixed, stained with crystal violet, and representative dishes are shown. c, KRAS-mutant lung cancer cell lines were treated with 25 nM of trametinib for 48 hr. Lysates were assayed by immunoblotting to determine the levels of ERK phosphorylation and total ERK. d, Schematic outline of the synthetic lethal RNAi screen for identifying sensitizers to MEK inhibition in KRAS-mutant lung cancer. A library pool of 3216 shRNAs targeting the human kinome was subcloned into the TRMPV backbone and retrovirally transduced into H23 cells, followed by neomycin selection. The selected cell population (T0) was then treated with doxycycline in the presence or absence of 25 nM trametinib for ten population doublings, followed by FACS isolation of Venus+/dsRed+ (shRNA expressing) cells (Tf). Genomic DNA isolated from T0 and Tf populations was used as a template for PCR amplification of shRNA guide strands, which were subjected to deep-sequencing to quantify the relative abundance of each shRNA in the library. e, Representation of the relative abundance of each shRNA in the library in vehicle- or trametinib-treated cells. shRNA abundance ratios were calculated as the number of reads after ten population doublings on doxycycline (Tf) divided by the number of reads before treatment (T0), and plotted as the mean of three replicates in ascending order. Positive control included shRNAs targeting Rpa1, Plk1, and CDK11a (Red circles). Negative control shRNAs targeted *renilla* luciferase (Green circles). f, Quantification of fluorescent cells in representative competitive proliferation assays in H23 cells transduced with the indicated shRNAs. The relative percentage of Venus+/dsRed+ cells was determined before (T0) and after ten population doublings on doxycycline (Tf) (results are relative to T0). The competitive assay was performed in the absence or presence of 25 nM of trametinib.

Administration: As used herein, the term "administration" refers to the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. For example, in certain embodiments, administration to an animal subject (e.g., to a human) may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

Agent: The term "agent" as used herein may refer to a compound or entity of any chemical class including, for example, polypeptides, nucleic acids, carbohydrates, lipids, small molecules, metals, and/or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. In some particular embodiments, an agent is or comprises a small molecule, an antibody, an antibody fragment, an aptamer, an siRNA, an shRNA, a DNA/RNA hybrid, an antisense oligonucleotide, a ribozyme, a peptide, a peptide mimetic, a peptide nucleic acid ("PNA") etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety. In some embodiments, an agent is provided and/or utilized in salt form.

Antiproliferative Agent: As used herein, the term "antiproliferative agent" refers to a substance that, when administered or applied to a source of dividing cells (e.g., a cell culture, a tissue sample, an organism, etc), reduces the extent (e.g., the number of cell doublings) and/or frequency (e.g., the rate of cell division events) of cell proliferation as compared with that observed under otherwise comparable conditions absence the antiproliferative agent.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Combination therapy: As used herein, the term "combination therapy" refers to those situations in which a subject is simultaneously exposed to two or more therapeutic regimens or modalities (e.g., to two or more therapeutic agents).

In some embodiments, two or more regimens or modalities are administered or applied simultaneously (e.g., one or more individual doses of each of two or more agents, may be administered at substantially the same time); in some embodiments, such regimens or modalities may be administered sequentially (e.g., at least a first dose of a first agent is administered prior to at least a first dose of a second agent); in some embodiments, such regimens or modalities such that individual doses or applications overlap.

Determine: Certain methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage form: and "unit dosage form", as used herein, the term "dosage form" refers to physically discrete unit of a therapeutic agent for a subject (e.g., a human patient) to be treated. Each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage administered to any particular patient will be selected by a medical professional (e.g., a medical doctor) within the scope of sound medical judgment.

Dosing regimen: (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously (e.g., by infusion) over a predetermined period. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Improve, increase, reduce, etc: As used herein, terms such as "improve", "increase", "reduce", etc., which necessarily imply a comparison, refer to a comparison with an appropriate comparable reference or standard. For example, in some embodiments, level and/or activity of an agent or marker of interest may be reduced under a set of conditions or circumstances of interest (e.g., after administration of therapy) as compared with its level and/or activity under a comparable set of conditions (e.g., prior to administration of the therapy or after administration of the therapy to an appropriate reference subject). In some embodiments, an appropriate reference may be a historical reference. In some embodiments, an appropriate reference may be an average, e.g., as may be observed within or across a relevant population.

Inhibition Therapy: As used herein, the term "inhibition therapy" refers to administration of therapy such that level and/or activity of a target is reduced (e.g., as compared with that observed under otherwise comparable conditions absent administration of the therapy). In some embodiments, inhibition therapy involves administration of an inhibitor agent. In some embodiments, an inhibitor agent is one whose presence, level, or form may correlate with inhibition (e.g., reduction in level and/or activity) of a target, as compared for example with that observed under otherwise comparable conditions absent the inhibitor agent. In some embodiments, an inhibitor agent is a direct inhibitor in that it directly binds to or interacts with a target. In some embodiments, an inhibitor is an indirect inhibitor in that it may not bind to or interact with the target itself, but rather may bind to or interact with another entity, with the result that level and/or activity of the target is reduced. To give but a few examples, where a target is or comprises a polypeptide, an inhibitor agent may, for example, bind to the polypeptide (e.g., so that interaction with a binding partner is inhibited), may bind to an interaction partner of the polypeptide (e.g., such that interaction is inhibited), may bind to a substrate or product of the polypeptide (e.g., so that frequency or extent of a reaction is inhibited), may bind to a regulator of the polypeptide (e.g., so that inhibition by the regulator is enhanced or activation by the regulator is reduced), may bind to a nucleic acid encoding the polypeptide (e.g., so that it's expression is reduced), or to an agent that directs or impacts expression or processing thereof, etc. In general, an inhibitor agent may be of any chemical class (e.g., may be or comprise a carbohydrate, an isotope, a lipid, a metal, a nucleic acid, a polypeptide, a small molecule, etc), and/or in some instances may be or comprise a virus or cell.

Receptor tyrosine kinase: The term "receptor tyrosine kinase", as used herein, refers to members of the protein family of receptor tyrosine kinases (RTK), which includes but is not limited to sub-families such as Epidermal Growth Factor Receptors (EGFR) (including ErbB1/EGFR, ErbB2/HER2, ErbB3/HER3, and ErbB4/HER4), Fibroblast Growth Factor Receptors (FGFR) (including FGF1, FGF2, FGF3, FGF4, FGF5, FGF6, FGF7, FGF18, and FGF21) Vascular Endothelial Growth Factor Receptors (VEGFR) (including VEGF-A, VEGF-B, VEGF-C, VEGF-D, and PlGF), RET Receptor and the Eph Receptor Family (including EphA1, EphA2, EphA3, EphA4, EphA5, EphA6, EphA7, EphA8, EphA9, EphA10, EphB1, EphB2. EphB3, EphB4, and EphB6).

Reduced Dosing: as used herein refers to administration of a reduced number of doses, reduced frequency of doses, and/or reduced magnitude of one or more doses relative to appropriate relevant reference regimen.

Reference: as used herein the term "reference" describes a standard, control, or other appropriate reference against which a comparison is made as described herein. For example, in some embodiments, a reference is a standard or control agent, animal, individual, population, sample, sequence, series of steps, set of conditions, or value against which an agent, animal, individual, population, sample, sequence, series of steps, set of conditions, or value of interest is compared. In some embodiments, a reference is tested and/or determined substantially simultaneously with the testing or determination of interest. In some embodiments, a reference is a historical reference, optionally embodied in a tangible medium. Typically, as would be understood by those skilled in the art, a reference is determined or characterized under conditions comparable to those utilized in the assessment of interest.

Refractory: As used herein, the term "refractory" refers to any subject or condition that does not respond with an expected clinical efficacy following the administration of provided compositions as normally observed by practicing medical personnel.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.*, 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Subject: as used herein, means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic regimen: A "therapeutic regimen", as that term is used herein, refers to a dosing regimen whose administration across a relevant population is or is expected to be correlated with a desired or beneficial therapeutic outcome.

Therapeutically effective amount: as used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

Protein Kinases and Malignancy

Protein kinases represent a large multigene family consisting of more than 500 proteins. Without wishing to be bound by any particular theory kinases can play a prominent role in the development and therefore treatment of a number of human diseases in oncology, neurology and immunology. Kinase function and expression is tightly regulated. In some embodiments, kinases can lead to proliferative disorders and/or malignancy due to, among other things, mutation, overexpression, over activation, or repression of activity.

Receptor Tyrosine Kinases

Receptor tyrosine kinases (RTKs) are cell surface receptors for, among other things, growth factors, cytokines, and hormones. In some embodiments, RTKs can regulate normal cellular processes. In some embodiments, RTKs can play a role in development and progression of many types of cancer.

Fibroblast growth factor receptors (FGFR) are a family of RTKs. FGFR family members often differ from one another, amongst other things, in their ligand affinities and tissue distribution. A full-length representative protein for example consists of an extracellular region, composed of three immunoglobulin-like domains, a single hydrophobic membrane-spanning segment and a cytoplasmic tyrosine kinase domain. The extracellular portion of the protein interacts with, amongst other things, fibroblast growth factors, often setting in motion a cascade of downstream signals, ultimately influencing, among other things, mitogenesis and differentiation.

Ras Network Components and Signaling

In some embodiments, proteins that can regulate the activity of kinases can include members of the Ras superfamily. The Ras superfamily can include but is not limited to Ras, Rho, Ran, Rab and Arf Without wishing to be bound by any particular theory these family members share a common domain which provides GTPase and nucleotide exchange activity. In some embodiments, the Ras protein subfamily includes KRAS, NRAS, and HRAS. In some embodiments, the Ras subfamily plays a role in regulation of cell proliferation. In some embodiments, mutations in Ras subfamily proteins can lead to constitutively active proteins. In some embodiment the constitutive activity can lead to cancer.

In some embodiments, members of the Ras superfamily can regulate the activity of mitogen-activated protein kinases (MAPK) which are also or formerly known as extracellular signal-related kinases (ERK). In some embodiments, this can be referred to as the Ras/MAPK signaling pathway. Without wishing to be bound by any particular theory regulation of MAP kinase activity can occur as a result of a signaling cascade that is initiated by a molecule or extracellular ligand activating a receptor at the surface of a cell. In some embodiments, the receptor can be a receptor tyrosine kinase (RTK). In some embodiments, activation of the RTK leads to autophosphorylation which can promote binding of guanine nucleotide exchange factors (GEF) to the RTK. In some embodiments, binding of the GEF to a phosphorylated RTK leads to activation of the GEF which can promote the removal of GDP from a member of the Ras subfamily allowing the Ras subfamily member protein to bind GTP and become active. In some embodiments, the active Ras subfamily member phosphorylates a member of the Raf kinase family. In some embodiments the Raf kinase family can include A-Raf, B-Raf, and C-Raf. In some embodiments, Raf kinase family members can phosphorylate, amongst other things, MEK. In some embodiments phosphorylated MEK can activate downstream MAPK/ERKs.

FGFR1

Fibroblast growth factor receptor 1 (FGFR1), a member of the FGFR family, also known as basic fibroblast growth factor receptor 1, fms-related tyrosine kinase-2, and CD331, has ligands which are, among other things, members of the fibroblast growth factor family.

Somatic mutations and/or gene amplifications of FGFR1 occur in several diseases including breast and lung cancers. Amplified expression of FGFR1 is generally associated with poor prognosis and relapse in cancer patients. Amplification of FGFR1 is a feature in 20% of lung cancer patients. Chromosomal translocations can also be a factor in FGFR1's involvement in cancer.

In some embodiments, the role of FGFR1 in cancer is abetting cancer progression and metastasis. Fibroblast growth factors can trigger the autophosphorylation of FGFR1 at important tyrosine residues within the activation loop of the tyrosine kinase domain. This autophosphorylation, among other things, results in a change of the structural conformation of the tyrosine kinase domain from an inactive form to an active one. Activated tyrosine kinase domains can phosphorylate tyrosine residues at other sites in FGFR1 along with FGFR1-bound adaptor protein. Phosphorylation of tyrosine residues at the C-terminal region of FGFR1 allows for recruitment and activation of phospholipase Cγ (PLCγ). This can lead to catalysis and transformation of phosphatidylinositol diphosphate (PIP2) to diacylglycerol (DAG) and inositol triphosphate (IP3). In some embodiments, FGFR1 signaling concurrently activates both Ras-MAPK/ERK and PI3K pathways. Both these pathways play a role in the proliferation and survival of cancer cells.

Fibroblast growth factor signals can be propagated downstream into the RAS-MAPK or PI3K-AKT signaling cascades. In some embodiments, this signal propagation is conducted by FGFR1-bound adaptor proteins. In some embodiments, fibroblast growth factor receptor substrate 2 (FRS2) serves as an adapter protein that links activated fibroblast growth factor receptors to downstream signaling pathways. FRS2 proteins act as docking proteins downstream of certain species of RTKs, including FGF receptors, neurotrophin receptors, RET, and ALK. FRS2 proteins bind to these RTKs via the PTB domain and become phosphorylated on tyrosine residues upon activation of these RTKs.

FGFR1 can phosphorylate FRS2. Phosphorylated FRS2 binds the adapter protein Growth factor receptor bound 2 (GRB2) and the Protein tyrosine phosphatase, non-receptor type (SHP-2). In a FGFR1/FRS2 signaling pathway, SHP-2 can act as a adapter protein. Shc and GRB2 can form a complex with the Guanine nucleotide exchange factor Son of sevenless protein (SOS). Translocation of this complex to the plasma membrane by binding to phosphorylated FRS2 allows SOS to activate v-Ha-ras Harvey rat sarcoma viral oncogene homolog (H-Ras) by GTP exchange due to its close proximity to membrane-bound H-Ras. Once in the active GTP-bound state, H-Ras interacts with several effector proteins, including v-Raf-1 murine leukemia viral oncogene homolog 1 (c-Raf-1). That results in activation of the Mitogen-activated protein kinase kinases 1 and 2 (MEK1/2)/Mitogen-activated protein kinases 1 and 3 (ERK1/2) signaling cascade. This cascade leads to phosphorylation of the target transcription factor ELK1.

Additionally, when GRB2 is bound to tyrosine-phosphorylated FRS2, the C-terminal SH3 domain of GRB2 can form a complex with the proline-rich region of GRB2-associated binding protein 1 (GAB1) to serve as an interface between these two docking proteins. Phosphatidylinositol-3-kinase kinase (PI3K) is one of the effectors of GAB1 and thus can be involved in FGF-induced activation of PI3K. Assembly of a FRS2/GRB2/GAB1 complex induced by FGF stimulation can lead to activation of PI3K and downstream effector proteins.

KRAS and Cancer

Without wishing to be bound by any particular theory KRAS is a member of the Ras family that is implicated in the development of cancers. In some embodiments, oncogenic point mutations in KRAS contribute to the formation of a large proportion of human tumors. Oncogenic KRAS mutations often compromise the GTPase activity of the protein, causing accumulation of KRAS in the active GTP-bound state and hyperactivation of KRAS effectors that can initiate and maintain malignant transformations. In some embodiments, oncogenic mutations in KRAS are found in 25-35% of lung adenocarcinomas. in some embodiments, mutations in the KRAS protein can lead to the development of, among other things, lung cancer, pancreatic cancer, colorectal cancer, endometrial cancer, biliary malignancy, cervical cancer, bladder cancer, liver cancer, leukemia, and breast cancer.

Without wishing to be bound by any particular theory, despite our understanding of RAS biology, cancer patients harboring KRAS mutations are currently treated with cytotoxic chemotherapies that are rarely effective. As the MAPK/ERK signaling pathway has been shown to be critical for the initiation and maintenance of KRAS mutant tumors in experimental systems, targeting downstream MAPK/ERK signaling effectors, such as MEK kinases, has been proposed as an alternative strategy to potentially manage KRAS-mutant tumors. In some embodiments the present disclosure recognizes that although MEK inhibitors show significant antitumor activity in $BRAF^{V600E}$ tumors and newer inhibitors produce a more effective ERK signaling inhibition through blocking MEK feedback reactivation mediated by CRAF, effectiveness of MEK inhibitors is marginal in KRAS-mutant cancers.

Treatment of Cancer and Development of Resistance

In some embodiments, therapeutic interventions for cancer are targeted to, among other things, inhibit protein kinase expression or activity. In some embodiments, therapeutic interventions for cancer are targeted to, among other things, proteins that can regulate the expression or activity of kinases. In some embodiments, proteins that can regulate the expression or activity of kinases can be, among other things, receptors or enzymes.

In some embodiments, treatment of cancers with protein kinase inhibitor therapy (e.g., via administration of protein kinase inhibitors) can lead to resistance. In some embodiments, this resistance can arise from mutations in kinases. In some embodiments, resistance can result from feedback activation loops. In some embodiments, a feedback activation loop results from targeted inhibition of selective kinases increasing expression or activity of other kinases that regulate tumor growth or survival. Among other things the present invention recognizes a need for additional therapeutic options including therapeutics treating those cancers that have developed resistance to a therapeutic. In some particular embodiments the present invention makes the unexpected observation that treatment of cancer with inhibitors targeting kinases in the same signaling pathway can result in synergistic inhibition of tumor growth or tumor volume.

In some embodiments, the present invention recognizes that resistance to treatment of a tumor with inhibitors of MEK can result from increased expression or activity of RTKs. In some embodiments, the present invention recognizes that treatment of a cancer which has developed resistance to inhibitors of MEK with a therapeutic agent that inhibits a RTK and a therapeutic agent that inhibits a mitogen activated kinase can result in reduced tumor growth or tumor volume. In some embodiments, the MEK inhibitor can be Trametinib In some embodiments, the RTK can be a member of the FGFR family. In some embodiments, the inhibitor of the RTK can be Ponatinib, BGJ398 or AZD4547. In some embodiments the inhibitors can be administered in combination at reduced dosing.

In some embodiments the present invention recognizes that increased expression or activity of RTKs can be utilized to identify subjects that would benefit from treatment with an RTK inhibitor. The present invention recognizes that subjects that have been treated with a MEK inhibitor may have developed resistance to a MEK inhibitor due to increased expression or activity of RTKs. In some embodiments measuring expression of RTKs on the surface of cells subsequent to a subjects treatment with a MEK inhibitor RTK Inhibition Therapy In some embodiments the present disclosure provides, among other things, therapeutic regimens that comprise administering RTK inhibition therapy to subjects, e.g., to cancer patients. In some embodiments, such cancer patients will be receiving, will have received, and/or will be scheduled to receive one or more chemotherapy regimens. In some embodiments, such cancer patients will be receiving, will have received, and/or will be scheduled to receive one or more mitogen activated (MAK) kinase therapies.

In general, RTK inhibition therapy is any therapeutic modality or regimen whose administration to a subject acts as an inhibitor of RTK (i.e., results in reduction in level and/or activity of ZDHHC9). Those skilled in the art will appreciate that, in some embodiments, a particular therapeutic modality or regimen may be considered to be RTK inhibition therapy if it has been demonstrated to achieve statistically significant RTK inhibition when administered to a relevant population; demonstration that RTK inhibition actually occurs, or occurs to a particular degree in each or any specific individual to whom the therapy is administered is not required.

In some embodiments, RTK inhibition therapy can be achieved by an RTK inhibitory agent. In some embodiments, an RTK inhibitory agent can be any class of agent. In some embodiments, an RTK inhibitory agent can be, among other things, a nucleic acid, an antibody, or a small molecule. In some embodiments, an RTK inhibitory agent may target two or more RTKs. In some embodiments, an RTK inhibitory agent may target one RTK. In some embodiments, an RTK inhibitory agent may be a potent inhibitor of two or more RTKs. In some embodiments, an RTK inhibitory agent may a potent inhibitor of one RTK. In some embodiments, an RTK inhibitory agent may target FGFR1. In some embodiments, an RTK inhibitory agent may target FGFR1 and one or more other RTKs.

EXEMPLIFICATION

Example 1: RTK and MEK Signaling in Cancer

The present Example describes studies demonstrating that KRAS-mutant lung cancers, which are notoriously difficult to treat and specifically are known to develop resistance to MEK inhibition, achieve such resistance, at least in part, through reactivation of ERK signaling. Thus, the present Example highlights a dependency of KRAS-mutant cancers on MAPK signaling pathway, and identifies the source of a problem associated with traditional MEK inhibition strategies for treatment of at least these tumors. The present Example specifically demonstrates that ERK-dependent feedback inhibition of FGFR1 activity mediates the unresponsiveness of KRAS-mutant lung cancers to MEK inhibition. The present Example therefore supports and confirms provided strategies for treatment of KRAS-mutant tumors (e.g., KRAS-mutant lung tumors) as described herein, including for example through combination therapy regimens in which MEK inhibitor therapy is combined with therapy that suppresses reactivation of ERK signaling and/or otherwise reduces resistance to MEK inhibitor therapy. In some embodiments, MEK inhibitor therapy is combined with therapy that inhibits one or more aspects of the same biological pathway; in some embodiments, MEK inhibitor therapy is combined with therapy that targets FGFR1 activity.

To understand the molecular mechanism that mediates the resistance of KRAS-mutant tumors to MEK inhibition, the sensitivity of BRAF and KRAS-mutant cancers of multiple lineages to MEK inhibitors was determined using the Genomic of Drug Sensitivity in Cancer (GDSC) dataset.

Among other things, as described herein, it was found that BRAF-mutant tumor cells were significantly more sensitive to multiple MEK inhibitors such as AZD6244 (selumetinib), PD0325901, and RDEA119 than tumor cells harboring oncogenic mutations in KRAS (FIG. 1a and Supplementary FIG. 1a). We confirmed the mutation-dependent sensitivity to MEK inhibition in lung cancer cells, one of the most prevalent and lethal cancer types, where KRAS is mutated in up to 30%. Consistently, we observed that the sensitivity of BRAF and KRAS-mutant lung cancer cells in in vitro clonogenic assays recapitulates the clinical experience, with KRAS-mutant cells being more resistant to effective doses of new MEK inhibitor Trametinib than were BRAF-mutant cells (FIG. 1b, c and Supplementary FIG. 1b, c).

Without wishing to be bound by any particular theory, we propose that differential sensitivity between BRAF and KRAS-mutant lung cancer cells to MEK inhibition may reflect the fact that mutant KRAS signals through multiple downstream effectors, whereas BRAF mediates its oncogenic effects mainly through MEK.

Figure 6:
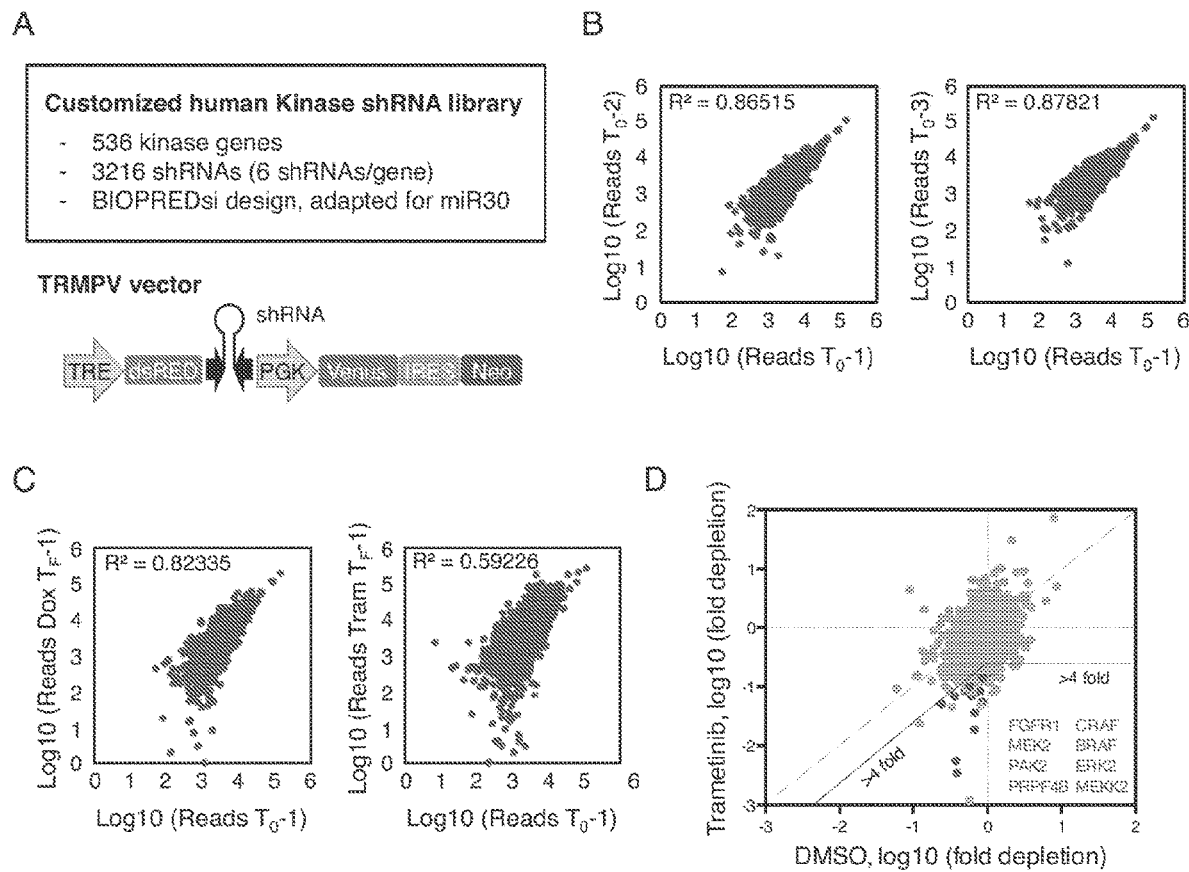
FIG. 6 shows A synthetic lethal RNAi screen identifies FGFR1 and MAPK effectors as sensitizers to MEK inhibition in KRAS-mutant lung cancer cells. a, Library features and schematic of the TRMPV-Neo vector. b, c, Representative scatter plots illustrating the correlation of normalized reads per shRNA between replicates at the beginning of the experiment (b) and replicates at different time points (c). d, H23 cells treated with trametinib (25 nM) were compared to those treated with DMSO to determine the fold change in shRNA abundance. Two shRNAs for FGFR1, CRAF, BRAF, ERK2, and MEKK2 were identified as selectively depleted in trametinib-treated cells as compared to DMSO-treated cells.
Figure 7:
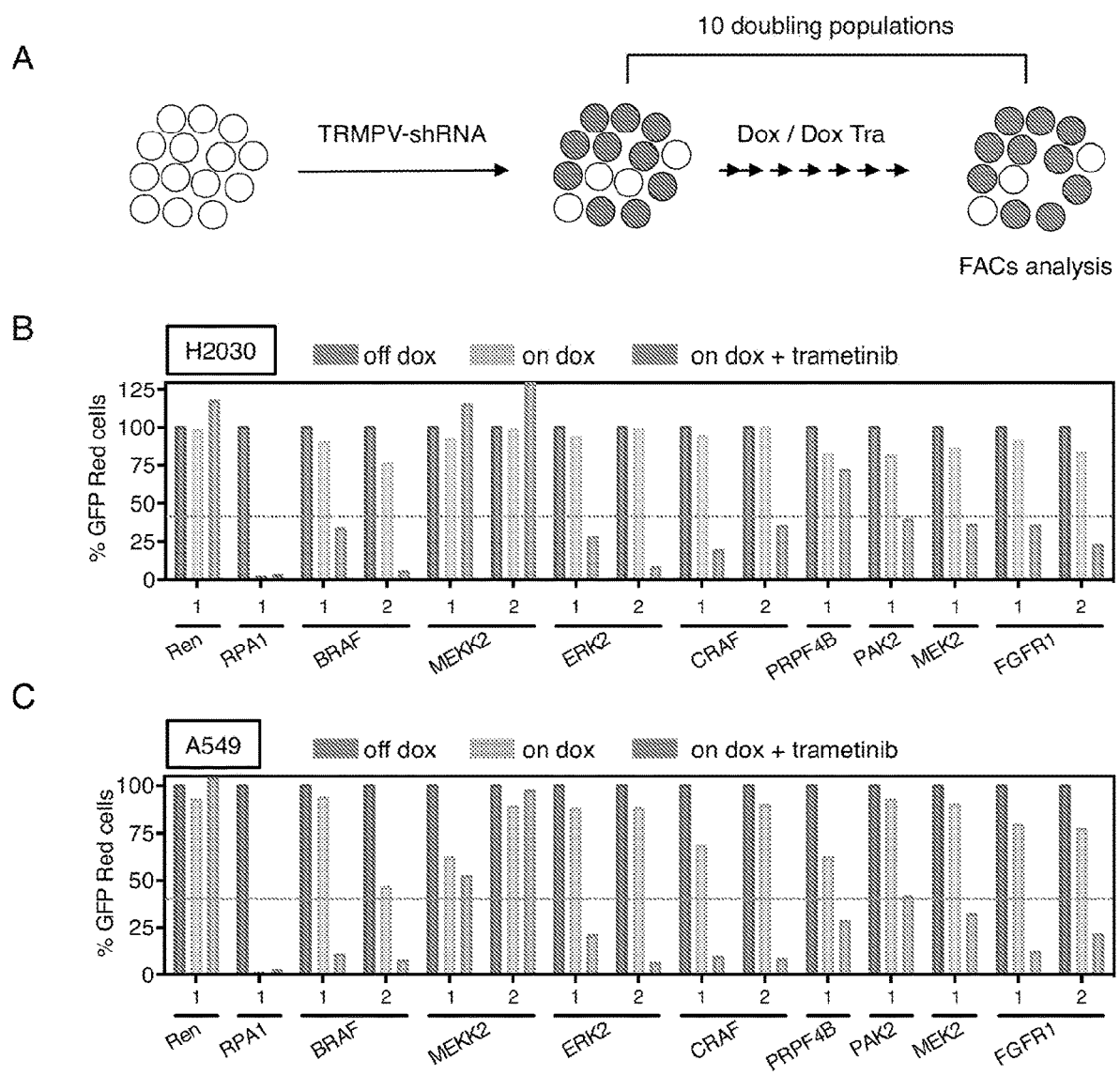
FIG. 7. Shows suppression of FGFR1 and MAPK effectors reduces the proliferation and viability of KRAS-mutant lung cancer cells treated with trametinib. a, Schematic of competitive proliferation assays. b, c, Quantification of fluorescent cells in representative competitive proliferation assays in H2030 and A549 cells transduced with the indicated shRNAs. The relative percentage of Venus+/dsRed+ cells was determined before (T0) and after ten population doublings on doxycycline (Tf) (results are relative to T0). The competitive assay was performed in the absence or presence of trametinib (25 nM).
Figure 8:
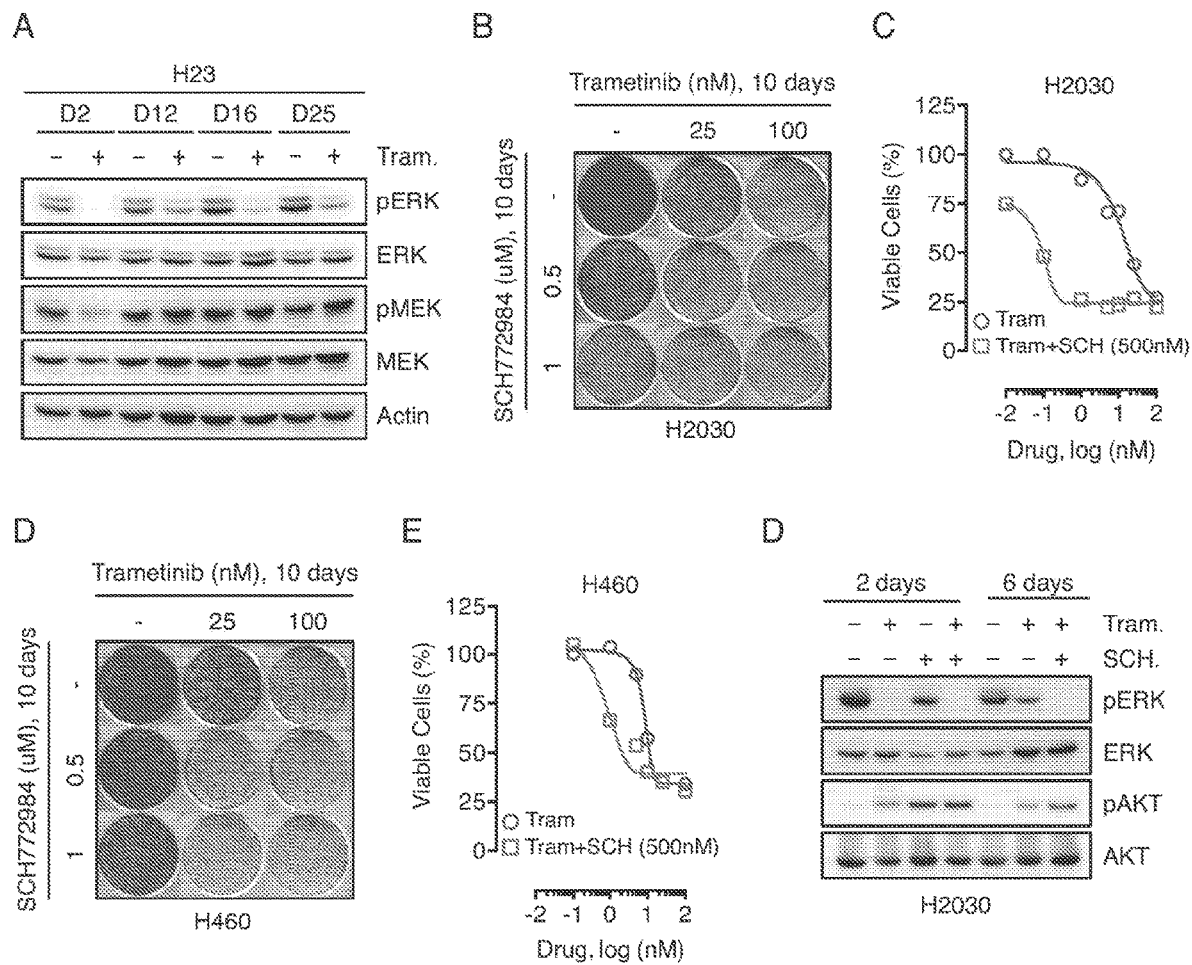
FIG. 8 shows ERK inhibitor SCH772984 enhances the antiproliferative effects of trametinib in KRAS-mutant lung cancer cells.a, H23 cells were treated with 25 nM of trametinib for 2, 12, 16, and 25 days. Lysates were assayed for immunoblot with the indicated antibodies b, d, Clonogenic assay of H2030 (b) and H460 (d) cells treated with increasing concentrations of trametinib, ERK inhibitor SCH772984, or their combination as indicated. Cells were fixed, stained with crystal violet, and photographed. A representative example of three independent experiments is shown. c, e, Cell viability of H2030 (c) and H460 (e) cells treated with increasing doses of trametinib alone or cotreatment with 500 nM of SCH772984 for 10 days. d, H2030 cells were treated with trametinib (25 nM), SCH772984 (500 nM), or their combination for the times shown. H2030 cells were pretreated with trametinib for 4 days, followed by treatment with SCH772984 for 2 days. Lysates were subjected to immunoblot analysis with the indicated antibodies.
Figure 21:
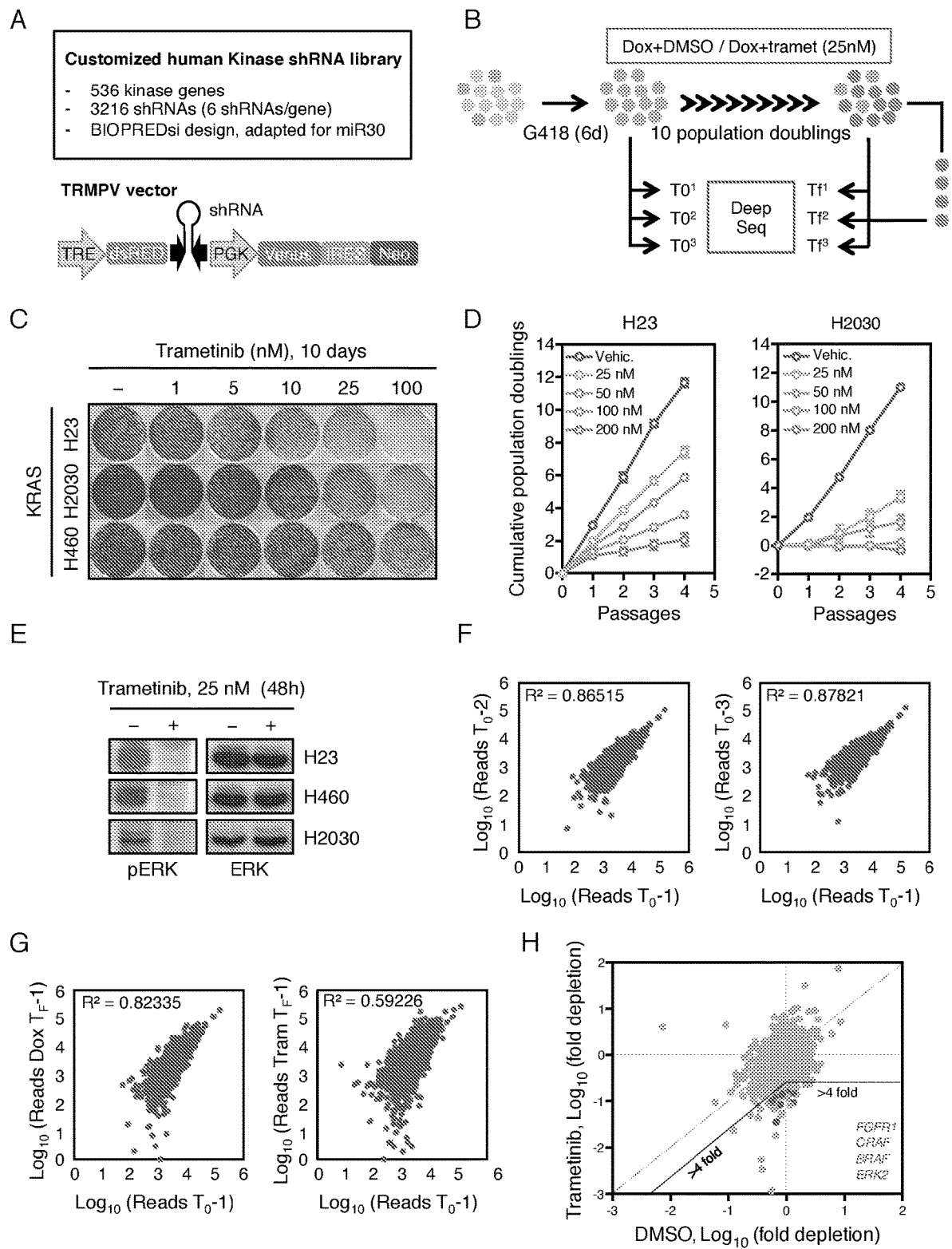
FIG. 21. Further illustrates suppression of FGFR1 and MAPK signaling effectors sensitize KRAS-mutant lung tumors to MEK inhibition. a, Library features and schematic of the TRMPV-Neo vector. b, Schematic outline of the synthetic lethal RNAi screen for identifying sensitizers to MEK inhibitor trametinib in KRAS-mutant lung cancer cells. c, Clonogenic assay of KRAS-mutant lung cancer cell lines (H23, H460, and H2030) cultured in the presence of increasing concentrations of trametinib for 10 days. A representative example of three independent experiments is shown. d, Proliferation assay of H23 and H2030 cells in the presence of increasing concentrations of trametinib for 4 passages. Data presented as mean of two independent experiments±s.d. e, KRAS-mutant lung cancer cell lines were treated with 25 nM of trametinib for 48 hr. Phospho and total levels of ERK were assayed by immunoblot. f, g, Representative scatter plots illustrating the correlation of normalized reads per shRNA between replicates at the beginning of the experiment (d) and replicates at different time points in the absence (left panel) or presence (right panel) of trametinib (25 nM) (e). h, H23 cells treated with trametinib (25 nM) were compared to those treated with DMSO to determine the fold change in the relative abundance of each shRNA in the library after ten population doublings on doxycycline. Two shRNAs for FGFR1, CRAF, BRAF, and ERK2 were identified as selectively depleted in trametinib-treated cells.

As described herein, we have identified genes whose inhibition sensitizes KRAS-mutant lung cancer cells to Trametinib. We built a custom shRNA library targeting the full complement of 536 human kinases (human kinome). This library, containing 3216 shRNAs (6 shRNA per gene), was cloned into the tet-responsive miR30-based TRMPV backbone, a vector optimized for negative-selection RNAi screening, and was transduced into the Tet-on-competent KRAS-mutant lung cancer cell line H23 (FIG. 6a, FIG. 21 a). After selection with neomycin, H23 cells were treated with doxycycline (to allow shRNA induction) in the absence or presence of Trametinib, and changes in library representation were determined after ten population doublings by deep sequencing of shRNA guide strands amplified from genomic DNA of sorted shRNA-expressing cells (FIG. 1d). Using the scoring criteria of more than four-fold average depletion in three independent replicates of Trametinib treated cells, 96 shRNAs were strongly depleted. Consistently, shRNAs targeting essential genes (RPA1, PLK1, and CDK11a) were identified as significantly depleted in both vehicle and Trametinib-treated cells, whereas the relative representation of non-targeting control shRNAs remained unchanged (FIG. 1e and FIG. 6). Genes for which at least two shRNAs were selectively depleted upon MEK inhibition were individually validated using multiple KRAS-mutant lung cancer cell lines. shRNAs targeting BRAF, CRAF, ERK2, and FGFR1 were the most depleted in both the primary screen and validation stages, identifying these genes as top candidates genes in the screen (FIG. 1f, FIG. 7, FIG. 17b, and FIG. 22a).

The results of our screen show that knockdown of MAPK/ERK signaling effectors sensitizes KRAS mutant lung cancer cells to Trametinib. To address the molecular mechanism underlying the synergistic effect of inhibiting MEK and other MAPK/ERK pathway effectors, we tested the durability of ERK signaling inhibition over time in KRAS-mutant lung cancer cell lines treated with 25 nM of Trametinib. Although Trametinib has been reported to stably inhibit ERK signaling by blocking MEK feedback reactivation mediated by RAF, we observed increased ERK phosphorylation in all KRAS-mutant cell lines after 6-12 days of MEK inhibition (FIG. 2a, FIG. 8a, FIG. 17c, and FIG. 22a).

Figure 17:
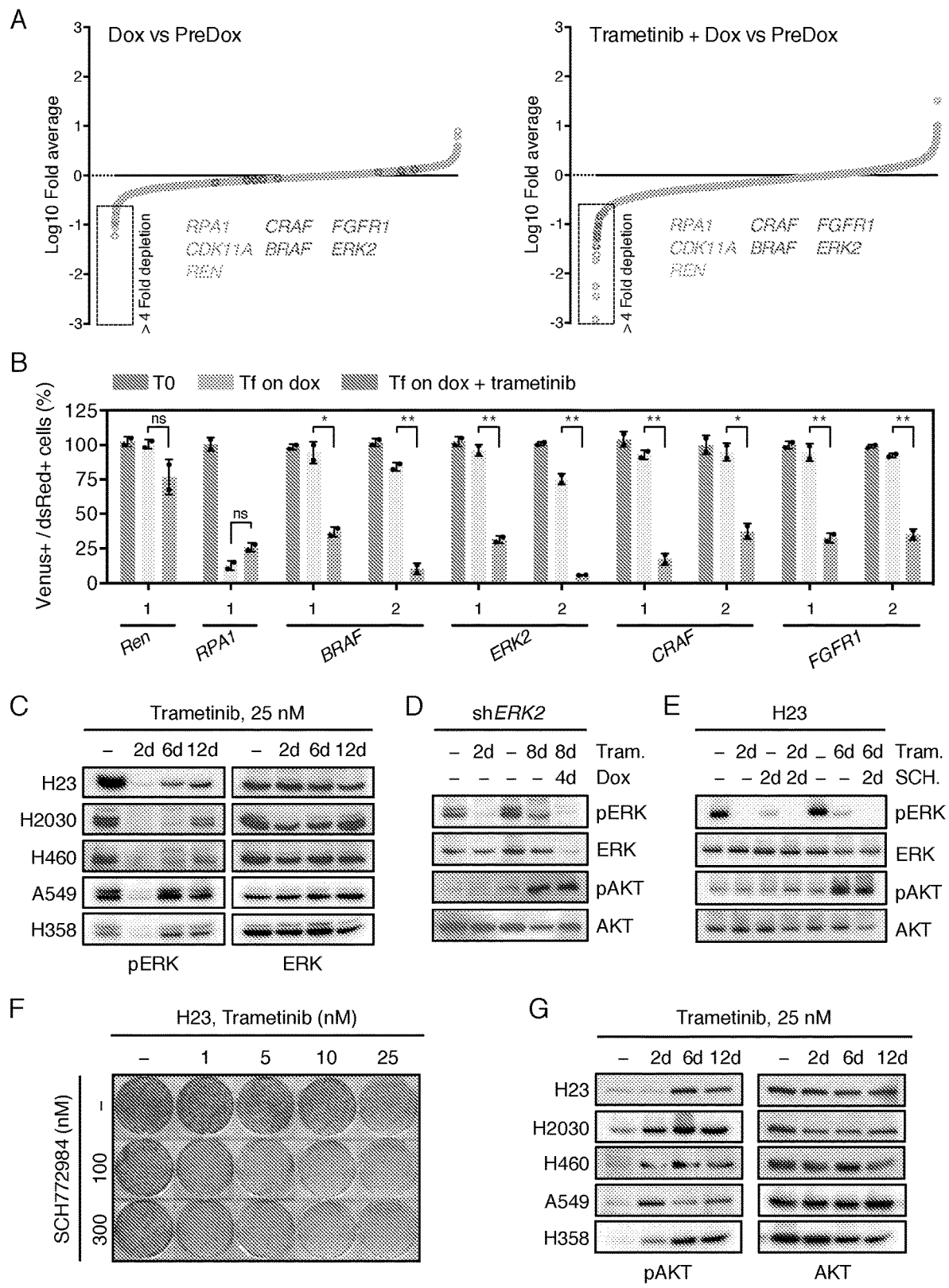
FIG. 17 further confirms suppression of different MAPK signaling effectors and FGFR1 sensitizes KRAS-mutant lung cancer cells to the MEK inhibitor trametinib. a, Representation of the relative abundance of each shRNA in the library in vehicle- or trametinib-treated H23 cells after ten population doublings on doxycycline. The mean of three (vehicle) and two (trametinib) replicates is plotted in ascending order. Positive control included shRNAs targeting RPA1 and CDK11A (Red circles). Negative control shRNAs targeted renilla (REN) luciferase (Green circles). b, Quantification of fluorescent cells in representative competitive proliferation assays in H23 cells transduced with non-targeting control (Ren) or the indicated shRNAs. The relative percentage of Venus+/dsRed+ cells was determined before (T0) and after ten population doublings on doxycycline (Tf) (results are relative to T0). The competitive assay was performed in the absence or presence of 25 nM of trametinib. Data presented as mean of two independent experiments±s.d. ns: not significant, *P<0.05, **P<0.01. c, KRAS-mutant lung cancer cell lines were treated with 25 nM trametinib for various times. The effect on ERK signaling was analyzed by immunoblot. d, H23 cells transduced with a doxycycline-inducible shRNA targeting ERK2 were treated with trametinib (25 nM) and doxycycline for the times shown. Lysates were assayed by immunoblot with the indicated antibodies. e, H23 cells were treated with trametinib (25 nM), SCH772984 (500 nM), or their combination for the times shown. H23 cells were pretreated with trametinib for 4 days, followed by treatment with SCH772984 604 and trametinib for 2 days. Lysates were subject to immunoblot analysis with the indicated antibodies. f, Clonogenic assay of H23 cells treated with increasing concentrations of trametinib, ERK inhibitor SCH772984, or their combination as indicated. A representative example of three independent experiments is shown. g, KRAS-mutant lung cancer cell lines were treated with 25 nM trametinib for various times. The effect on AKT signaling was analyzed by immunoblot.
Figure 22:
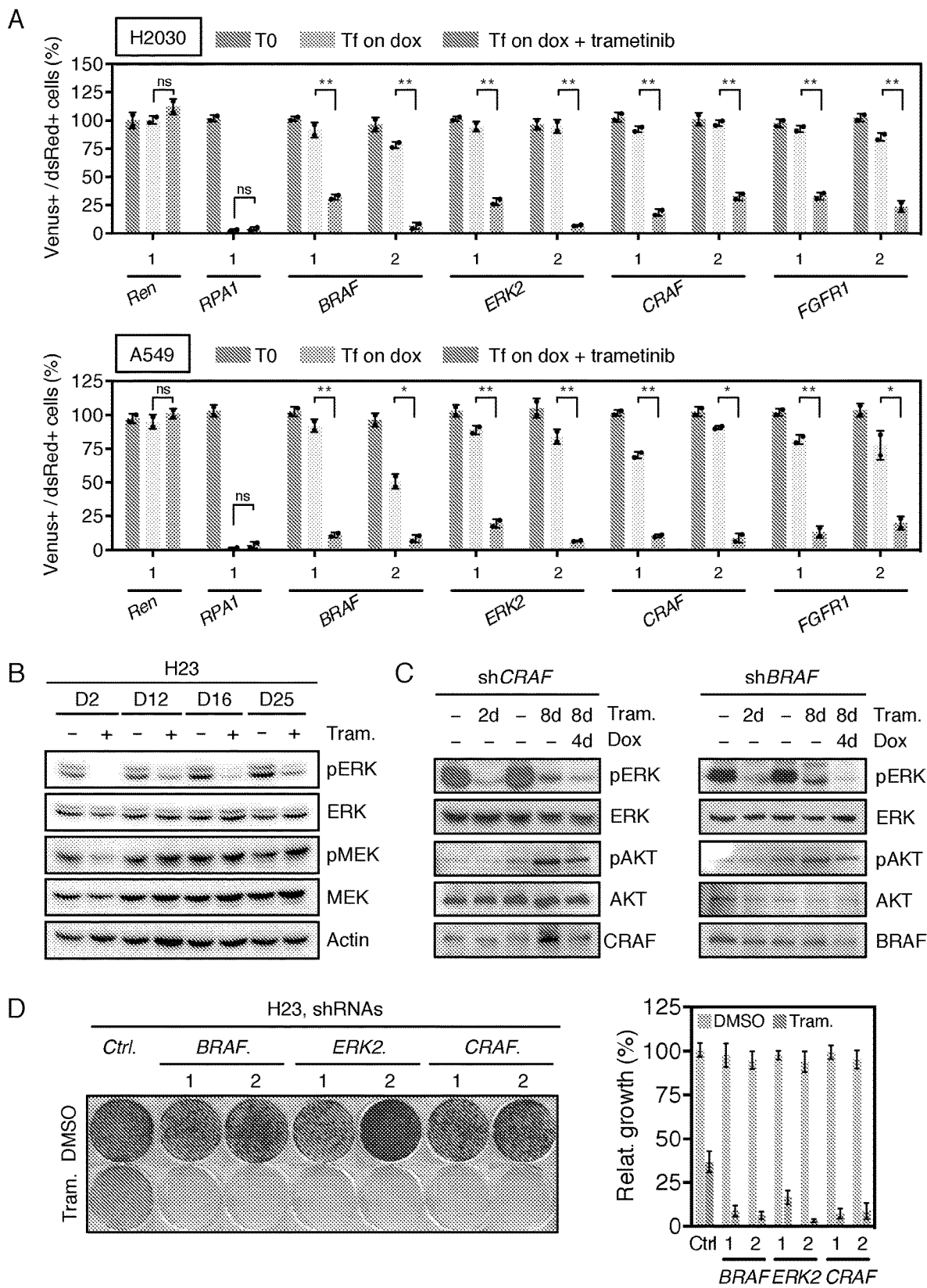
FIG. 22. Further documents that suppression of FGFR1 and different MAPK signaling effectors reduces the proliferation and viability of KRAS-mutant lung cancer cells treated with trametinib. a, Quantification of fluorescent cells in representative competitive proliferation assays in H2030 (upper) and A549 (lower) cells transduced with non-targeting control (Ren) or the indicated shRNAs. The relative percentage of Venus+/dsRed+ cells was determined before (T0) and after ten population doublings on doxycycline (Tf) (results are relative to T0). The competitive proliferation assay was performed in the absence or presence of trametinib (25 nM). Data presented as mean of two independent experiments±s.d. *P<0.05, **P<0.01. b, H23 cells were treated with trametinib (25 nM) for various times. Lysates were assayed by immunoblot with the indicated antibodies. c, H23 cells transduced with doxycycline-inducible shRNAs targeting CRAF and BRAF were treated with trametinib (25 nM) and doxycycline for the times shown. H23 cells were pretreated with trametinib for 4 days, followed by treatment with doxycycline and trametinib for 4 days. Lysates were assayed by immunoblot with the indicated antibodies. d, Clonogenic assay of H23 cells transduced with BRAF, CRAF, ERK2, and non-targeting control shRNAs. Cells were cultured with DMSO or trametinib (25 nM) for 10 days. Relative growth of DMSO-(light grey bars) and trametinib-treated cells (dark grey and medium grey bars) is shown (right). Data presented as mean of three independent experiments±s.d.
Figure 23:
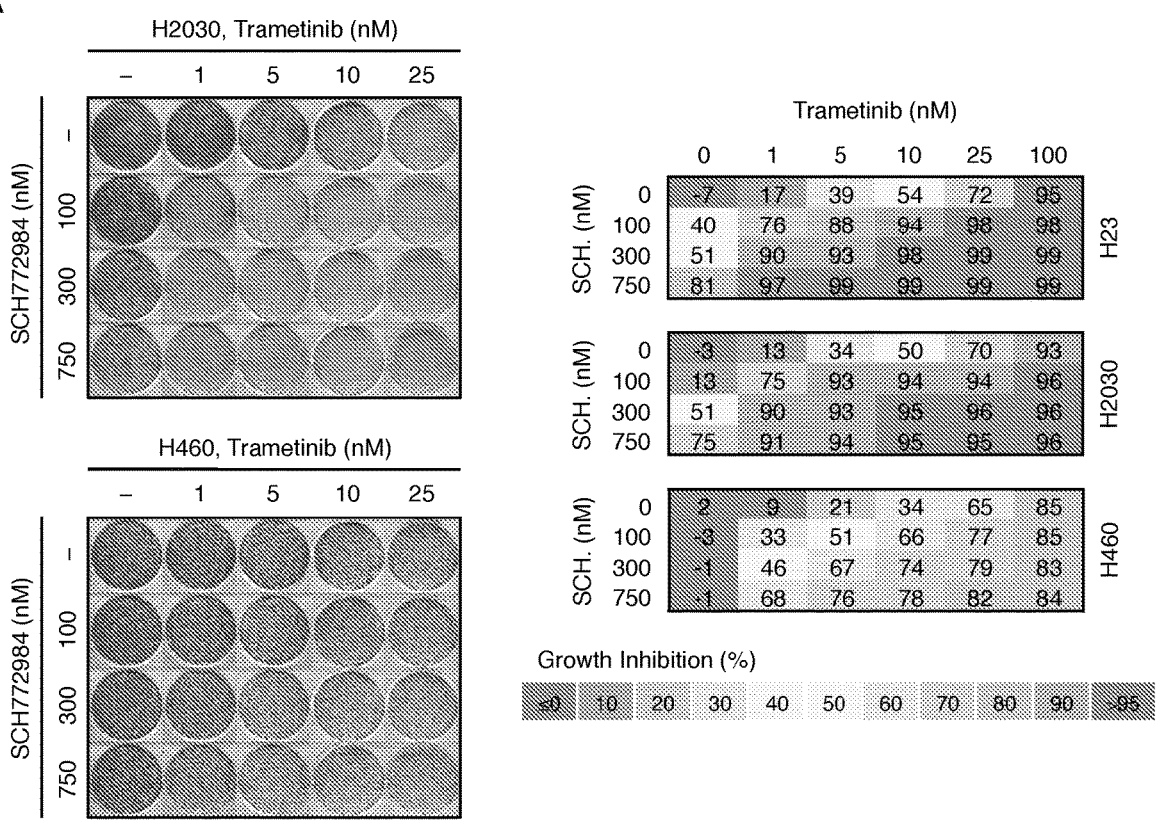
FIG. 23. Further documents ERK inhibitor SCH772984 enhances the antiproliferative effects of trametinib in KRAS-mutant lung cancer of trametinib in KRAS-mutant lung cancer cells. a, Clonogenic assay of H2030 (upper) and H460 (lower) cells treated with increasing concentrations of trametinib, ERK inhibitor SCH772984, or their combination as indicated. A representative example of three independent experiments is shown. Percent inhibition at each concentration of the drug in H23, H2030, and H460 cells is presented (right). Data presented as mean of three independent experiments. b, H2030 cells were treated with trametinib (25 nM), SCH772984 (500 nM), or their combination for the times shown. H2030 cells were pretreated with trametinib for 4 days, followed by treatment with SCH772984 and trametinib for 2 days. The effect on ERK and AKT signaling was analyzed by immunoblot. c, Cell viability of H23, H2030, and H460 cells treated with increasing doses of trametinib, ERK inhibitor SCH772984, or their combination for 10 days. Data presented as mean of three independent replicates±s.d. The concentration of trametinib that inhibited cell proliferation by 50% (GI50) was calculated in the absence or the presence of increasing concentrations of SCH772984 (bottom).
Figure 23:
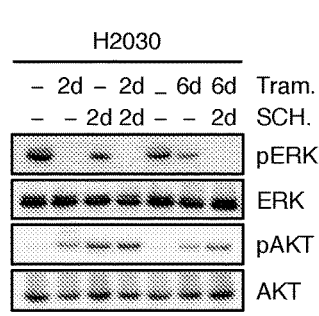
Figure 23:
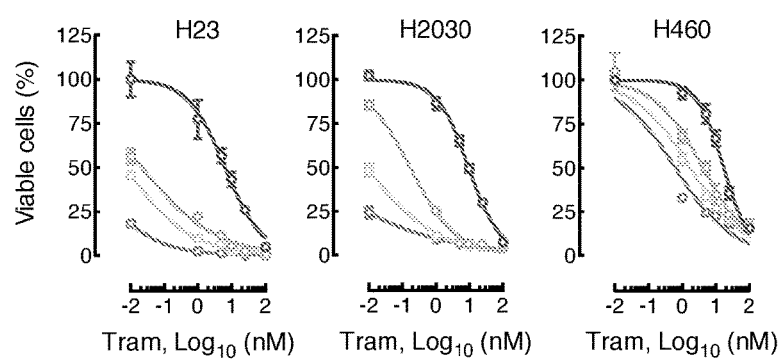
Figure 24:
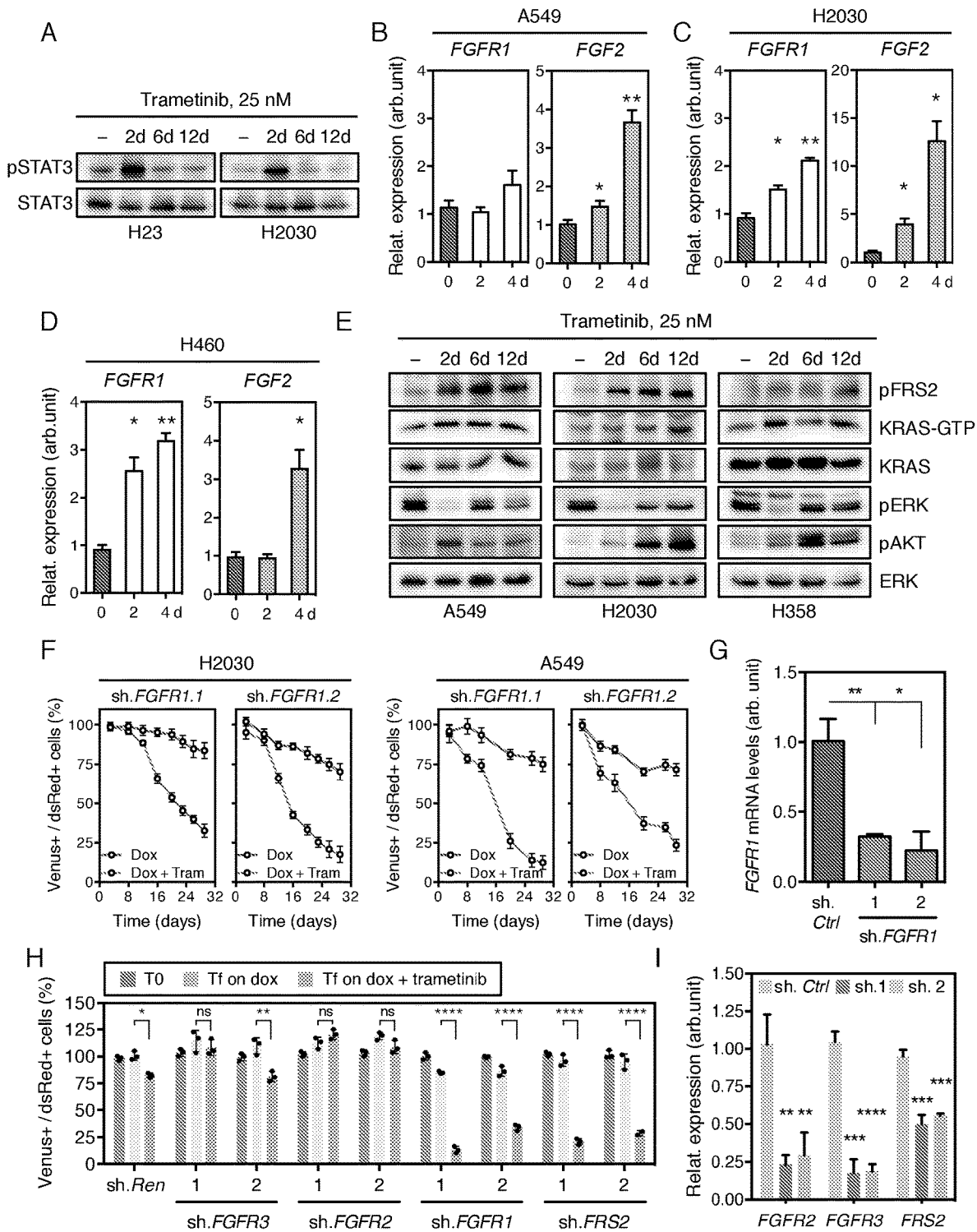
FIG. 24. Further illustrates feedback activation of FGFR1 signaling leads to adaptive resistance to trametinib in KRAS-mutant lung cancer cells. a, KRAS-mutant lung cancer cell lines H23 and H2030 were treated with 25 nM trametinib for various times. The effect on STAT3 signaling was analyzed by immunoblot. b, c, d, qRT-PCR 729 for FGFR1 and FGF2 in A549 (b), H2030 (c) and H460 (d) cells treated with trametinib for the indicated times. Data presented as mean normalized for FGFR1 and FGF2 expression±s.d. *P<0.05, **P<0.01. e, A549, H2030, and H358 cells were treated with trametinib (25 nM) for various times. Lysates were subject to immunoblot analysis with the indicated antibodies. f, Quantification of fluorescent cells in representative competitive proliferation assays in H2030 and A549 cells transduced with FGFR1 shRNAs. The relative percentage of Venus+/dsRed+ cells was determined at day 2 and at different time points during ten population doublings on doxycycline±trametinib (25 nM) (results are relative to day 2). Data presented as mean of three independent experiments±s.d. g, qRT-PCR for FGFR1 in H23 cells transduced with non-targeting control and FGFR1 shRNAs. Data presented as mean normalized for FGFR1 expression±s.d. *P<0.05, **P<0.01. h, Quantification of fluorescent cells in representative competitive proliferation assays in A549 cells transduced with non-targeting control (Ren) or the indicated shRNAs. The relative percentage of Venus+/dsRed+ cells was determined before (T0) and after ten population doublings on doxycycline (Tf) (results are relative to T0). The competitive assay was performed in the absence or presence of 25 nM of trametinib. Data presented as mean of three independent experiments±s.d. *P<0.05, P<0.01, P<0.0001. i, qRT-PCR for FGFR2, FGFR3, and FRS2 in A549 cells transduced with non-targeting control, FGFR2, FGFR3 and FRS2 shRNAs. Data presented as mean normalized for FGFR2, FGFR3, and FRS2 expression±s.d. P<0.01, *P<0.001, **P<0.0001.

Similar combined effects were observed after co-treatment of KRAS-mutant lung cancer cells with trametinib and the ERK inhibitor SCH772984 (FIG. 17 e, f, and FIG. 23). These observations underscore the marked dependency of KRAS-mutant tumors on the MAPK signaling pathway and show that targeting the pathway at different points can achieve sustained ERK inhibition. In addition to producing a rebound in MAPK signaling, prolonged exposure of KRAS-mutant cells to trametinib also caused compensatory activation of the PI3K and JAK/STAT pathways as assessed by AKT and STAT3 phosphorylation, respectively (FIG. 17d, e, g and FIG. 22c, 3b, 4a). Although the increase in STAT3 phosphorylation was transient and returned to baseline after several days (FIG. 24a, FIG. 19, and FIG. 26b), AKT phosphorylation was sustained (FIG. 17g). Unlike their effects on the rebound of ERK signaling, genetic or pharmacologic inhibition of MAPK signaling had little effect on trametinib-induced increases in pAKT (FIG. 17d, e, and FIG. 22c, 23b). The activation of multiple signaling pathways following trametinib-treatment of KRAS-mutant cells can be most easily explained by a relief in pleiotropic feedback mechanisms produced by constitutive RAS signaling.

Figure 2:
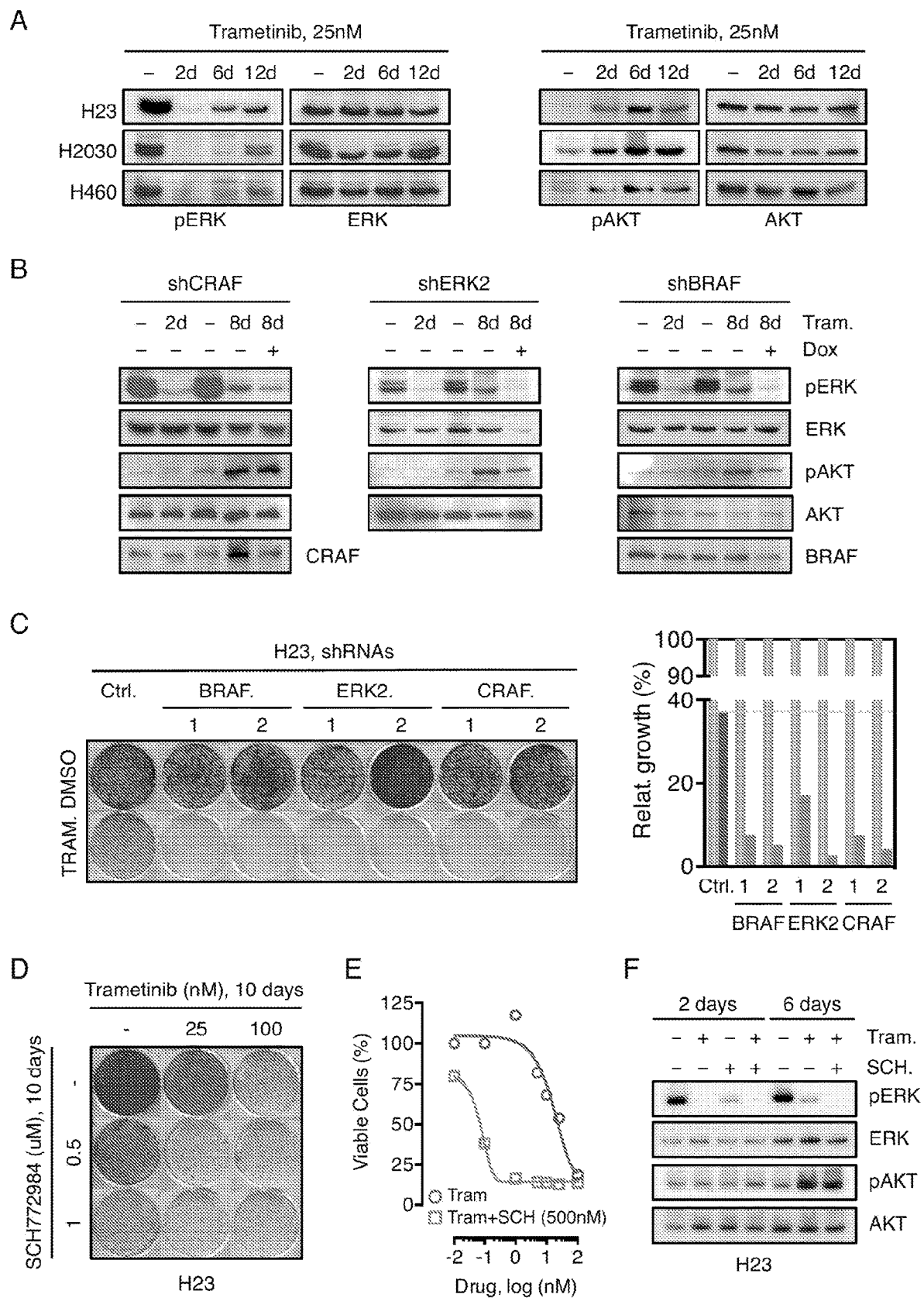
FIG. 2 shows reactivation of MAPK and PI3K signaling attenuates the effect of MEK inhibition in KRAS-mutant lung cancer. a, The indicated KRAS-mutant lung cancer cell lines were treated with 25 nM of trametinib for 2, 6, and 12 days. Lysates were assayed for immunoblot to determine the levels of ERK, AKT, phospho-ERK, and phospho-AKT. b, H23 cells transduced with doxycycline-inducible shRNAs targeting CRAF, ERK2, and BRAF were treated with 25 nM of trametinib for the times shown. Doxycycline (to induce shRNAs) was added after 4 days of treatment with trametinib to determine the requirement of CRAF, ERK2, and BRAF in the reactivation of MAPK and PI3K signaling following MEK inhibition. Lysates were subjected to immunoblot with the indicated antibodies. c, Clonogenic assay of H23 cells transduced with BRAF, CRAF, ERK2, and non-targeting control shRNAs. Cells were cultured in the presence of DMSO or 25 nM of trametinib for 10 days, and remaining cells were fixed, stained with crystal violet, and photographed. Relative growth of DMSO-(light grey bars) and trametinib-treated cells (dark grey and medium grey bars) was quantified by densitometry after extracting crystal violet from the stained cells using 10% of acetic acid. A representative example of three independent experiments is shown. d, Clonogenic assay of H23 cells treated with increasing concentrations of trametinib, ERK inhibitor SCH772984, or their combination as indicated. Cells were processed as described above. A representative example of three independent experiments is shown. e, Cell viability of H23 cells treated with increasing doses of trametinib alone or cotreatment with 500 nM of SCH772984 for 10 days. f, H23 cells were treated with trametinib (25 nM), SCH772984 (500 nM), or their combination for the times shown. H23 cells were pretreated with trametinib for 4 days, followed by treatment with SCH772984 for 2 days. Lysates were subjected to immunoblot analysis with the indicated antibodies.

ERK signaling rebound was accompanied with an activation of PI3K pathway as indicated by an increase in AKT phosphorylation, suggesting that substantial compensatory feedback mechanisms are induced by MEK inhibition in KRAS-mutant lung cancer cells (FIG. 2a, FIG. 17c). To test whether MAPK/ERK signaling effectors identified in the screen are required for the rebound in ERK phosphorylation observed following Trametinib treatment, we transduced H23 cells with doxycycline-inducible shRNAs targeting CRAF, BRAF, and ERK2. Knockdown of these ERK pathway effectors blocked the rebound in ERK phosphorylation at 8 days of Trametinib treatment, with minimal effect on AKT phosphorylation (FIG. 2b). Consistently, knockdown of CRAF, BRAF, and ERK2 enhanced the antiproliferative effects of Trametinib in clonogenic assays as compared to cells transduced with a non-targeting control shRNA, supporting the notion that rebound of ERK signaling counterbalances the antitumor effect of Trametinib in KRAS-mutant lung cancers (FIG. 2c, FIG. 18d, and FIG. 22c, d).

Figure 9:
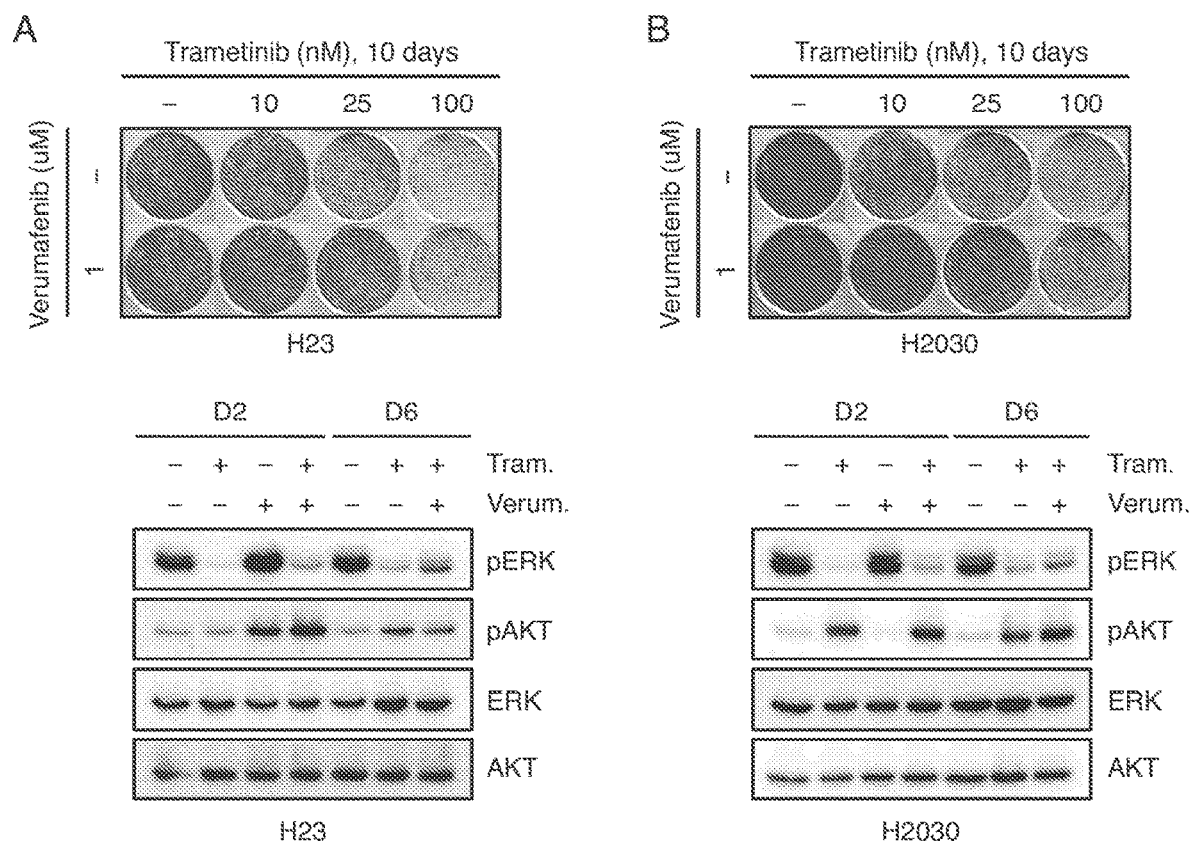
FIG. 9 shows b, Clonogenic assay of H23 and H2030 cells treated with increasing concentrations of trametinib, BRAF inhibitor verumafenib (1 µM), or their combination as indicated. Cells were fixed, stained with crystal violet, and photographed. A representative example of three independent experiments is shown. c, H23 and H2030 cells were treated with trametinib (25 nM), SCH772984 (1 µM), or their combination for the times shown. Cells were pretreated with trametinib for 4 days, followed by treatment with verumafenib for 2 days. Lysates were subjected to immunoblot analysis with the indicated antibodies.

We examined whether pharmacologic inhibition of RAF and ERK kinases recapitulate the enhanced antiproliferative effects of BRAF, CRAF or ERK2 knockdown in Trametinib-treated KRAS-mutant lung cancers. To date, multiple BRAF inhibitors are clinically available, whereas ERK inhibitors are still under preclinical development. Co-treatment of KRAS-mutant lung cancers with Trametinib and the BRAF inhibitor verumafenib resulted in a significant reduction in the antiproliferative effects of Trametinib compared to cells treated with Trametinib alone. Without wishing to be bound by any particular theory, we propose that this paradoxical effect is a consequence of enhanced ERK signaling in cells treated with the drug combination and it is consistent with the properties of BRAF inhibitors to transactivate RAF dimers in the context of wild-type BRAF cells (Supplementary FIG. 4b, c, FIG. 23). In contrast, co-treatment with Trametinib and the experimental ERK inhibitor SCH772984 prevented pERK rebound and produced a more complete inhibition of ERK signaling than Trametinib alone, providing a rationale for the cooperation observed in the clonogenic assays (FIG. 2d, e, f, FIG. 9, FIG. 17 e,f,g). Together, these results indicate that reactivation of ERK signaling mediates, at least in part, the resistance of KRAS-mutant lung cancers to MEK inhibition, highlighting the dependency of KRAS-mutant cancers on MAPK signaling pathway.

Figure 3:
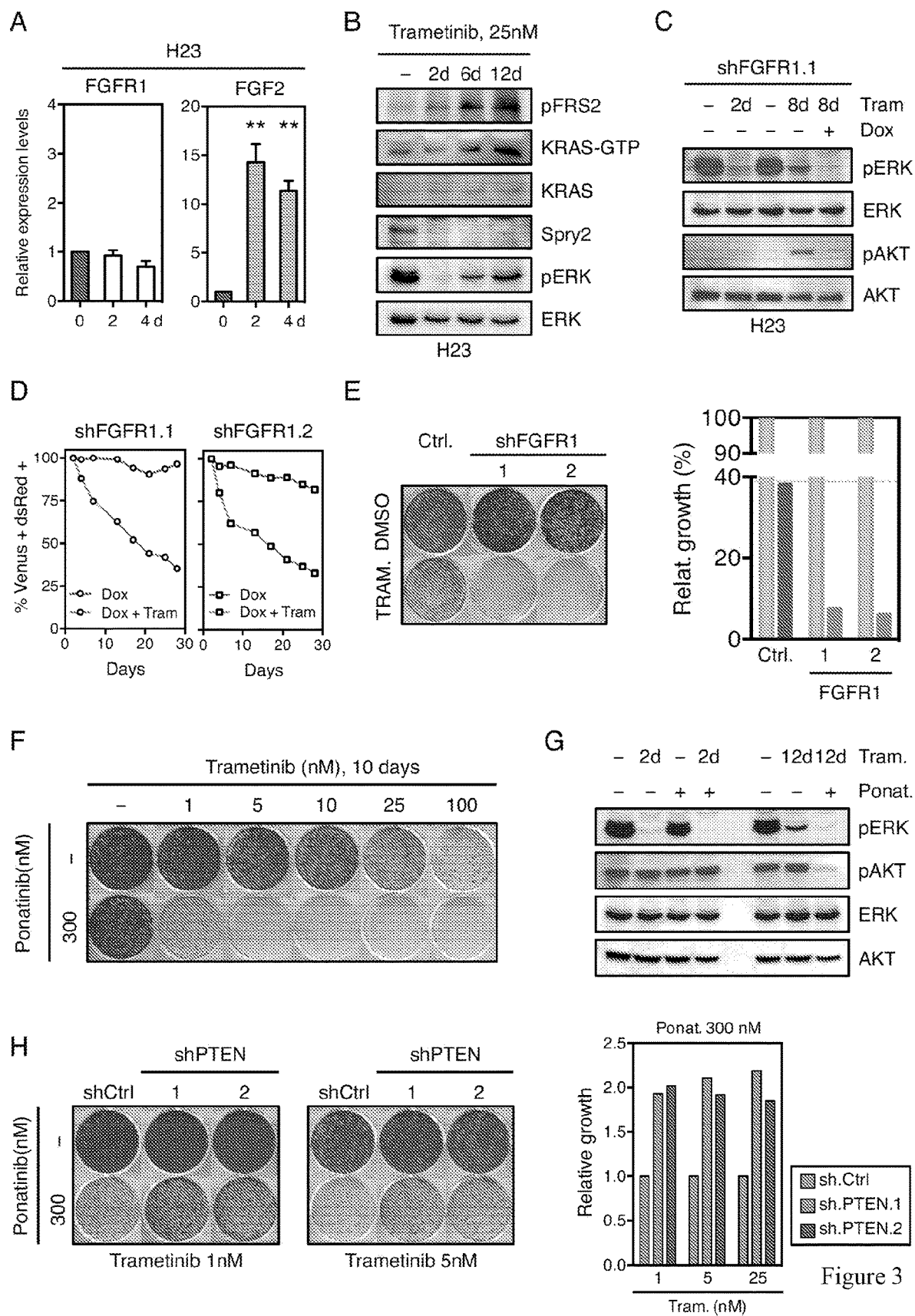
FIG. 3. Shows targeting of FGFR1 efficiently inhibits MAPK and PI3K signaling reactivation following MEK inhibition. a, qRT-PCR for FGFR1 and FGF2 in H23 cells treated with trametinib for the indicated times. Data presented as mean normalized FGFR1 and FGF2 expression±SD. **p<0.01. b, H23 cells were treated with 25 nM of trametinib for 2, 6, and 12 days. Lysates were subjected to immunoblot with the indicated antibodies. c, H23 cells transduced with a doxycycline-inducible shRNA targeting FGFR1 were treated with 25 nM of trametinib for the times shown. Cells were pretreated with trametinib for 4 days, followed by treatment with doxycycline (to induce shRNA) for another 4 days. ERK, AKT, phospho-ERK, and phospho-AKT levels were detected by western blot. d, Quantification of fluorescent cells in representative competitive proliferation assays in H23 cells transduced with FGFR1 shRNAs. The relative percentage of Venus+/dsRed+ cells was determined at day 2 and at different time points during ten population doublings on doxycycline (results are relative to day 2). The competitive assay was performed in the absence and presence of trametinib (25 nM). e, Clonogenic assay of H23 cells transduced with FGFR1 and non-targeting control shRNAs. Cells were treated with DMSO or trametinib (25 nM) for 10 days, and remaining cells were fixed, stained with crystal violet, and photographed. Relative growth of DMSO-(light grey bars) and trametinib-treated cells (dark grey and medium grey bars) was quantified by densitometry after extracting crystal violet from the stained cells using 10% of acetic acid. A representative example of three independent experiments is shown. f, Clonogenic assay of H23 cells treated with increasing concentrations of trametinib alone or in combination with ponatinib (300 nM). Cells were processed as described above. A representative example of three independent experiments is shown. g, H23 cells were treated with trametinib (25 nM), ponatinib (300 nM), or their combination for the times shown. To detect the ability of ponatinib to inhibit the rebound in MAPK and PI3K signaling following MEK inhibition, H23 cells were pretreated with trametinib for 4 days, followed by treatment with ponatinib for 2 days. Lysates were subjected to immunoblot analysis with the indicated antibodies. h, Clonogenic assay of H2030 cells transduced with PTEN and non-targeting control shRNAs. Cells were treated with trametinib (1 and 5 nM) alone or in combination with ponatinib (300 nM) for 10 days, and remaining cells were processed and quantified as described above. A representative example of three independent experiments is shown.
Figure 10:
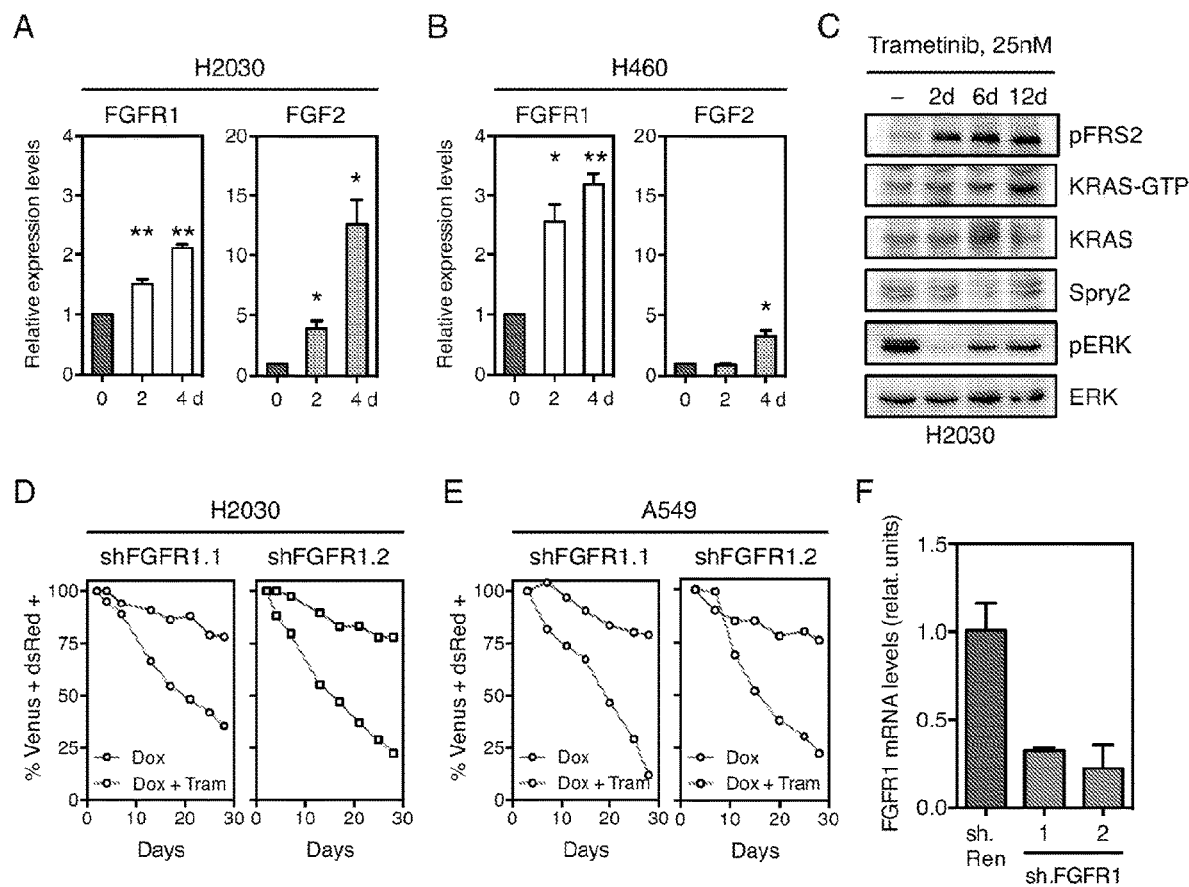
FIG. 10 shows feedback activation of FGFR1 mediates reactivation of MAPK and PI3K signaling in KRAS-mutant lung cancer cells treated with trametinib. a, b, qRT-PCR for FGFR1 and FGF2 in H2030 (a) and H460 (b) cells treated with trametinib for the indicated times. Data presented as mean normalized FGFR1 and FGF2 expression±SD. *p<0.05, **p<0.01. c, H2030 cells were treated with 25 nM of trametinib for 2, 6, and 12 days. Lysates were subjected to immunoblot with the indicated antibodies. d, e, Quantification of fluorescent cells in representative competitive proliferation assays in H2030 (d) and A549 (e) cells transduced with FGFR1 shRNAs. The relative percentage of Venus+/dsRed+ cells was determined at day 2 and at different time points during ten population doublings on doxycycline (results are relative to day 2). The competitive assay was performed in the absence and presence of trametinib (25 nM). f, qRT-PCR for FGFR1 in H23 cells transduced with non-targeting control and FGFR1 shRNAs.
Figure 18:
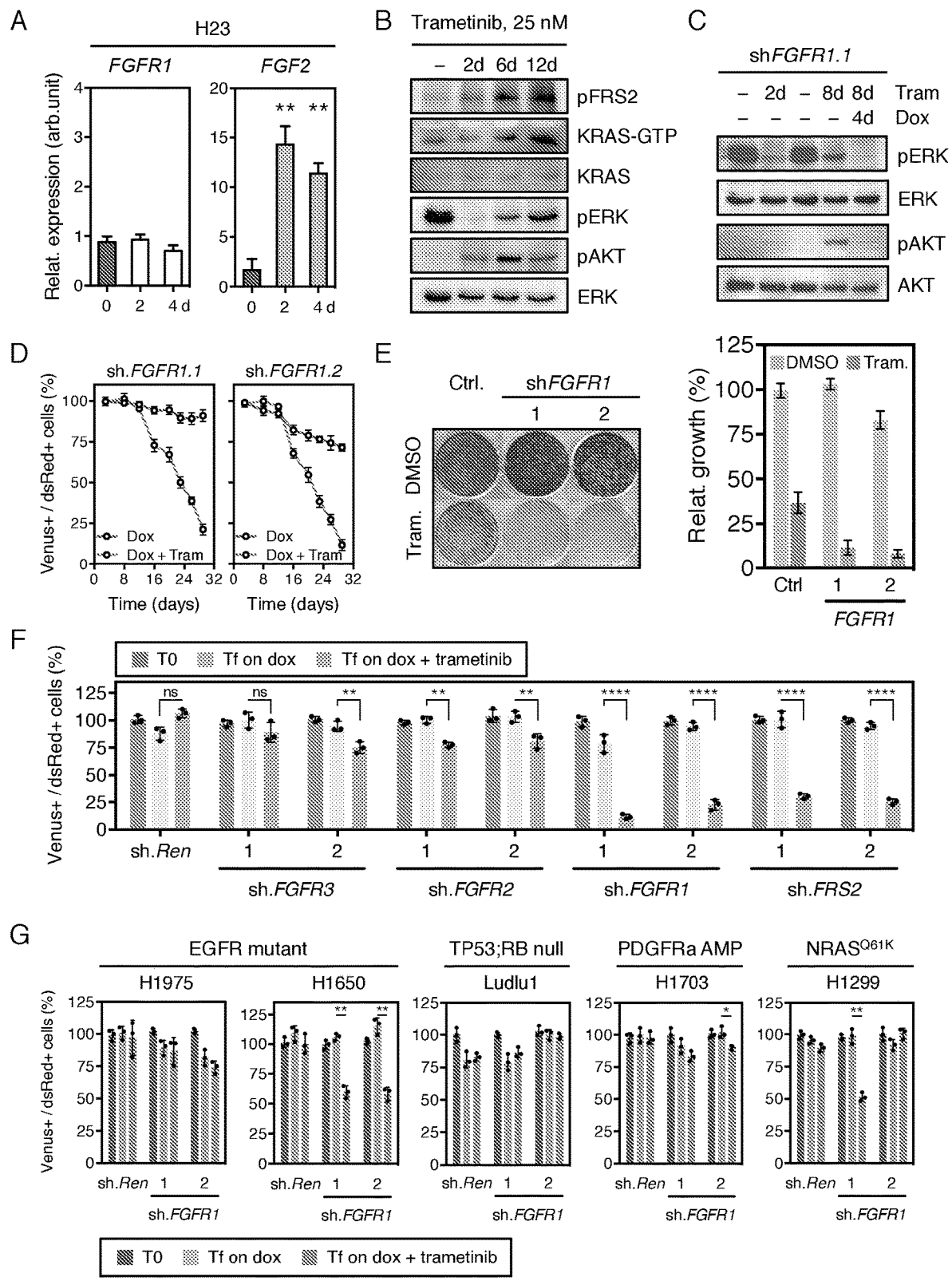
FIG. 18 further confirms feedback activation of FGFR1 via MAPK and PI3K signaling attenuates the effect of trametinib in KRAS-mutant lung cancer. a, qRT-PCR for FGFR1 and FGF2 in H23 cells treated with trametinib for the indicated times. Data presented as mean normalized for FGFR1 and FGF2 expression±s.d. **P<0.01. b, H23 cells were treated with 25 nM of trametinib for various times. Lysates were subject to immunoblot analysis with the indicated antibodies. c, H23 cells transduced with a doxycycline-inducible shRNA targeting FGFR1 were treated with trametinib (25 nM) and doxycycline for the times shown. The effect on ERK and AKT signaling was analyzed by immunoblot. d, Competitive proliferation assays in H23 cells transduced with doxycycline-inducible FGFR1 shRNAs. The relative percentage of Venus+/dsRed+ cells was determined at day 2 and at different time points for ten population doublings on doxycycline trametinib (25 nM) (results are relative to day 2). Data presented as mean of three independent experiments±s.d. e, Clonogenic assay of H23 cells transduced with FGFR1 and non-targeting control shRNAs. Cells were cultured with DMSO or trametinib (25 nM) for 10 days. Relative growth of DMSO-(light grey bars) and trametinib-treated cells (dark grey and medium grey bars) is shown (right). Data presented as mean of three independent experiments±s.d. f, g, Quantification of fluorescent cells in representative competitive proliferation assays in H23 (f) and the indicated lung cancer cells (g) transduced with doxycycline-inducible non-targeting control (Ren (Renilla)) or the indicated shRNAs. The relative percentage of Venus+/dsRed+ cells was determined before (T0) and after ten population doublings on doxycycline (Tf) (results are relative to T0). The competitive assay was performed in the absence or presence of 25 nM of trametinib. Data presented as mean of three independent experiments±s.d. ns: not significant, *P<0.05, P<0.01, **P<0.0001.

Feedback activation of RTKs following targeted inhibition of selective kinases has previously been reported to lead to drug resistance. As receptor tyrosine kinase FGFR1 was identified as one of the top candidate genes in our RNAi screen, we next investigated whether activation of FGFR1 signaling contributes to the resistance of KRAS-mutant lung cancers to MEK inhibition. Analysis of expression confirmed that FGFR1 and/or its ligand FGF2 were significantly upregulated in KRAS-mutant lung cancers upon treatment with Trametinib (FIG. 3a FIG. 10a, b, FIG. 18a, FIG. 24 b, c, d). Importantly, this upregulation resulted in increased phosphorylation of the downstream effector FRS2 (FIG. 3b, FIG. 18 FIG. 24), suggesting that MEK inhibition elicits a strong feedback activation of FGFR1 signaling. Activation of FGFR1 was accompanied by reduced levels of the negative regulator of RTK signaling Spry2, and correlated with increasing levels of RAS-GTP, activation of PI3K pathway, and rebound in ERK signaling (FIG. 3b and FIG. 10c). To determine whether feedback activation of FGFR1 signaling mediates the rebound of MAPK and PI3K pathways, H23 cells transduced with a doxycycline-inducible shRNA targeting FGFR1 were treated with Trametinib for 8 days and phospho-protein levels of ERK and AKT were determined at different time-points in the presence or absence of doxycycline. Knockdown of FGFR1 following 6 days of treatment with Trametinib blocked the rebound in both MAPK and PI3K signaling pathways as indicated by reduced levels of pERK and pAKT, respectively (FIG. 3c, FIG. 18c). Consistently, synergistic effect between knockdown of FGFR1 and MEK inhibition were observed in cell competition and long-term clonogenic assays (FIG. 3d, e FIG. 10d, e, f, FIG. 18 d,e, FIG. 24 f,g). Of note, suppression of FGFR1 minimally impacted the proliferation of vehicle-treated cells, suggesting that KRAS-mutant tumor cells are FGFR1 independent. Collectively, our data suggest that relief of ERK-dependent feedback inhibition of FGFR1 activity mediates the unresponsiveness of KRAS-mutant lung cancers to MEK inhibition.

Figure 25:
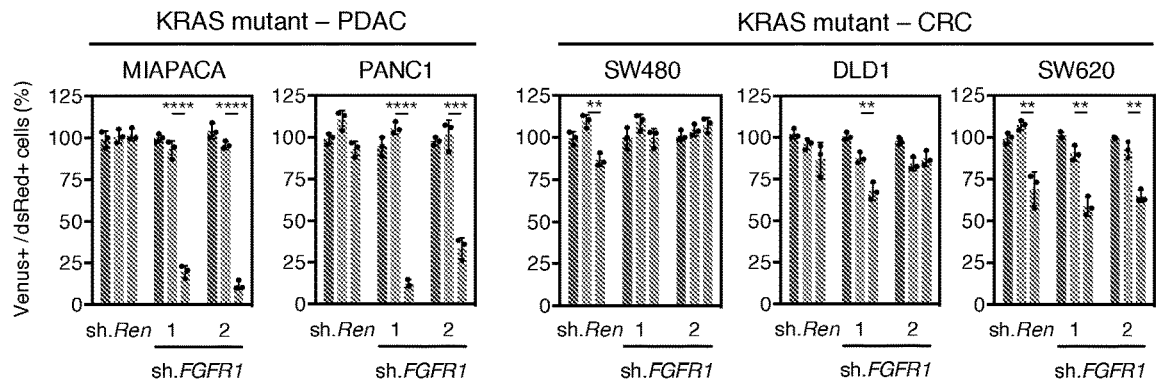
FIG. 25. Further illustrates increased phosphorylation of FRS2 following treatment with trametinib predicts sensitivity to FGFR1 suppression. a, Competitive proliferation assays in the indicated KRAS-mutant cancer cell lines transduced with doxycycline-inducible non targeting control (Ren) or FGFR1 shRNAs. The relative percentage of Venus+/dsRed+ cells was determined before (T0) and after ten population doublings on doxycycline (Tf) (results are relative to T0). The competitive assay was performed in the absence or presence of 25 nM of trametinib. Data presented as mean of three independent experiments±s.d. P<0.01, *P<0.001, ****P<0.0001. b, A panel of lung (H1975, H1650, Ludlu-1, H1703, and H1299), pancreas (MIAPACA, PANC1), and colorectal (SW620, SW480, and DLD1) cancer cell lines were treated with 25 nM trametinib for various times. Lysates were subject to immunoblot analysis with the indicated antibodies.
Figure 25:
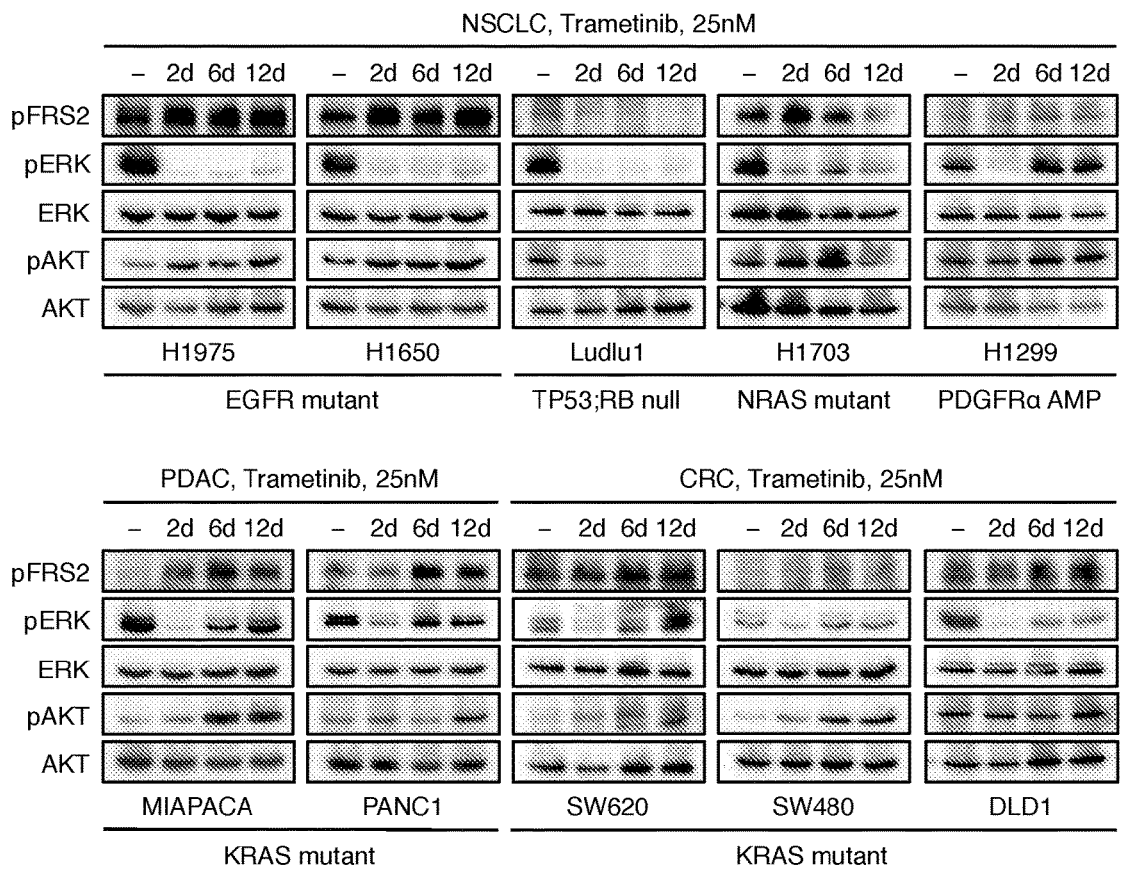

The ability of FGFR1 inhibition to sensitize cells to trametinib showed distinct specificities: for example, only shRNAs targeting FGFR1 or FRS2, but not those targeting family members FGFR2 and 3, sensitized KRAS-mutant lung cancer cells to trametinib (FIG. 18f and FIG. 24h, i). FGFR1 knockdown had little impact on trametinib sensitivity in KRAS wild-type lung cancer cells (FIG. 18g). Moreover, FGFR1 shRNAs also synergized with trametinib in KRAS mutant pancreatic cancer cells but not KRAS-mutant colorectal cancer cells (FIG. 25a). Importantly, cellular sensitivity to FGFR1 inhibition correlated with whether increased FRS2 phosphorylation occurred following trametinib treatment (FIG. 25b). Therefore, treatment of certain KRAS-mutant tumor types with trametinib induces a dependency on FGFR1 signaling that leads to adaptive drug resistance.

Figure 11:
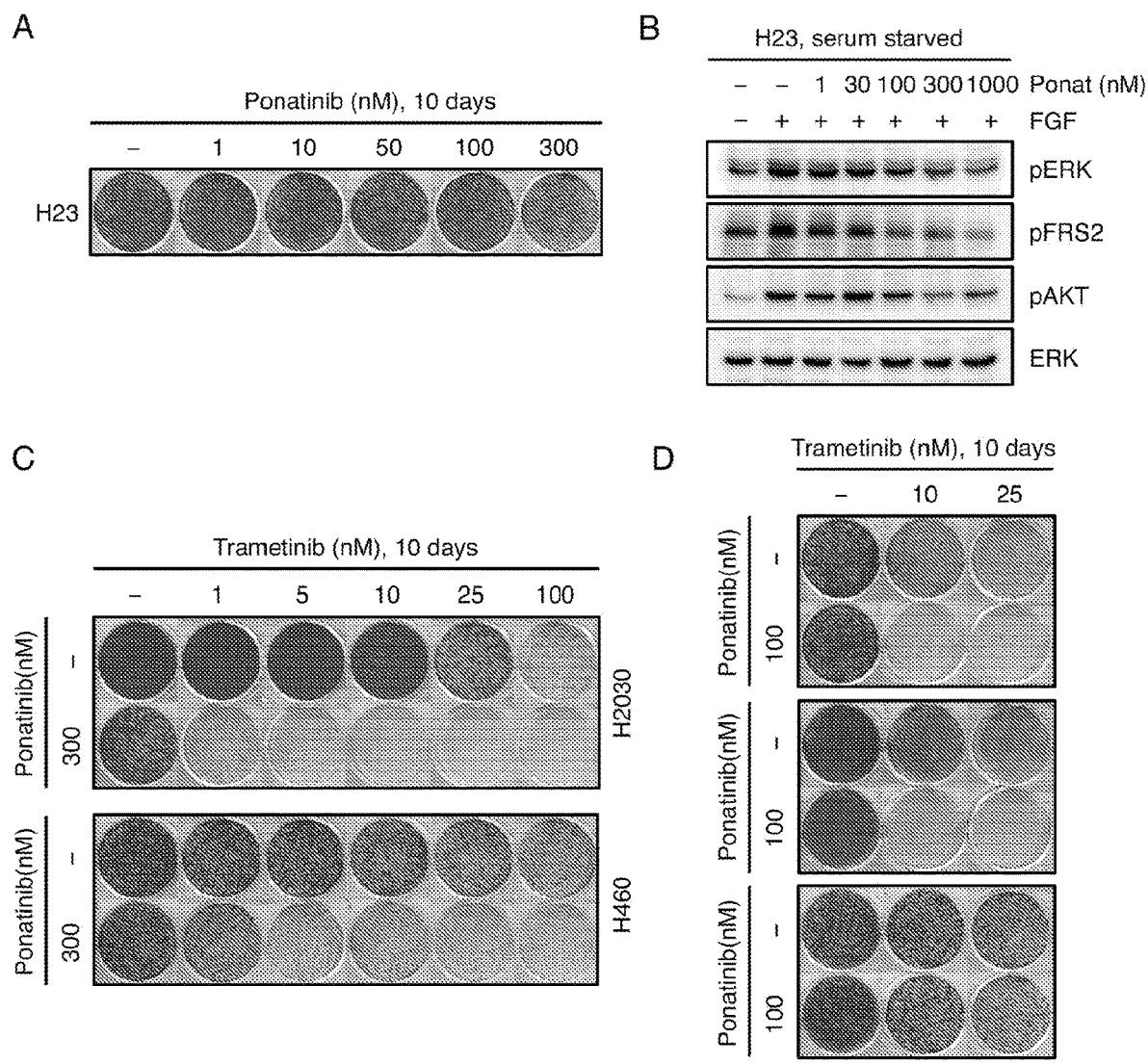
FIG. 11 shows pharmacological inhibition of FGFR1 enhances the antitumor effect of trametinib in KRAS-mutant lung cancer cells. a, Serum starved H23 cells were treated with FGF2 (50 ng/ml) and increasing concentration of ponatinib as indicated. Lysates were subjected to immunoblot with the indicated antibodies. b, Clonogenic assay of H23 cells treated with increasing concentrations of ponatinib. Cells were fixed, stained with crystal violet, and photographed. A representative example of three independent experiments is shown. c, d, Clonogenic assay of H23, H2030, and H460 cells treated with increasing concentrations of trametinib in the presence of 300 nM (c) and 100 nM (d) of ponatinib. Cells were processed as described above. A representative example of three independent experiments is shown.
Figure 12:
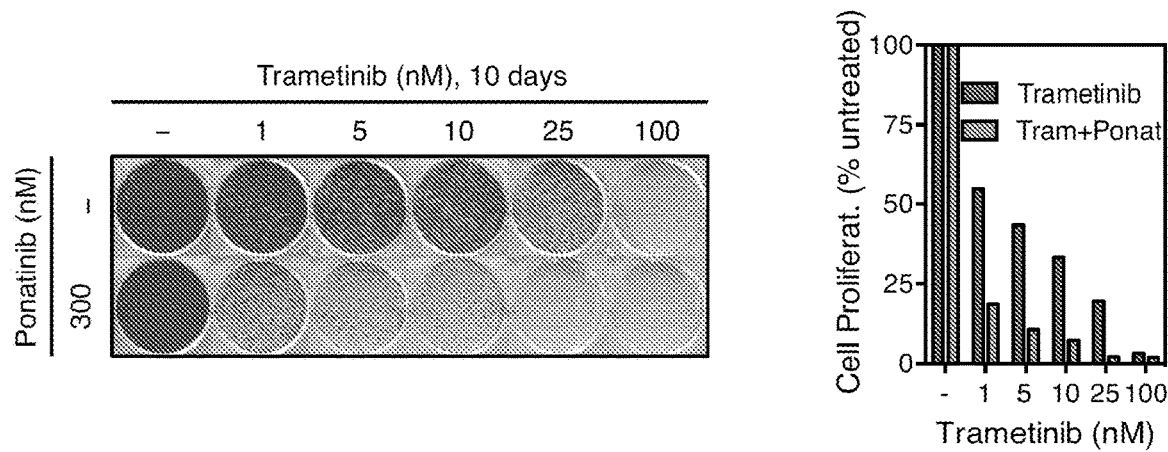
FIG. 12 shows inhibition of FGFR1 sensitizes murine KRAS-mutant lung cancer cells to MEK inhibition. Clonogenic assay of a murine lung cancer cell line harboring mutations in KRAS and p53. Tumor cells were treated with increasing concentrations of trametinib alone or in combination with ponatinib (300 nM). Cells were fixed, stained with crystal violet, and photographed. Relative cell growth was quantified by densitometry after extracting crystal violet from the stained cells using 10% of acetic acid. A representative example of three independent experiments is shown.
Figure 13:
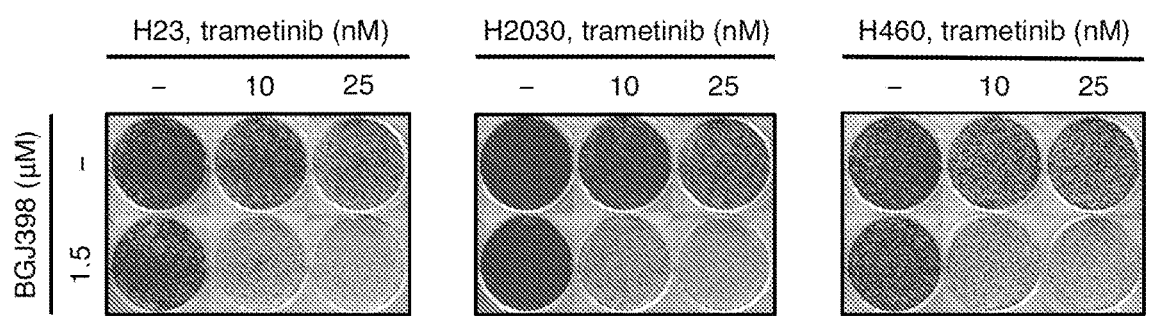
FIG. 13 shows BGJ398 and AZD4547 confer sensitivity to MEK inhibition in KRAS-mutant lung cancer. a, b, Clonogenic assay of H23, H2030, and H460 cells treated with increasing concentrations of trametinib alone and in combination with BGJ398 (1.5 µM) or AZD4547 (2 µM). Cells were fixed, stained with crystal violet, and photographed. A representative example of three independent experiments is shown.
Figure 13:
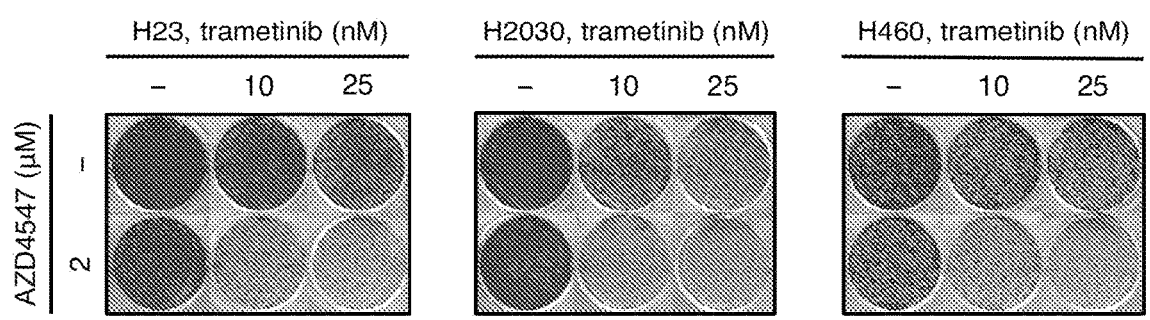
Figure 19:
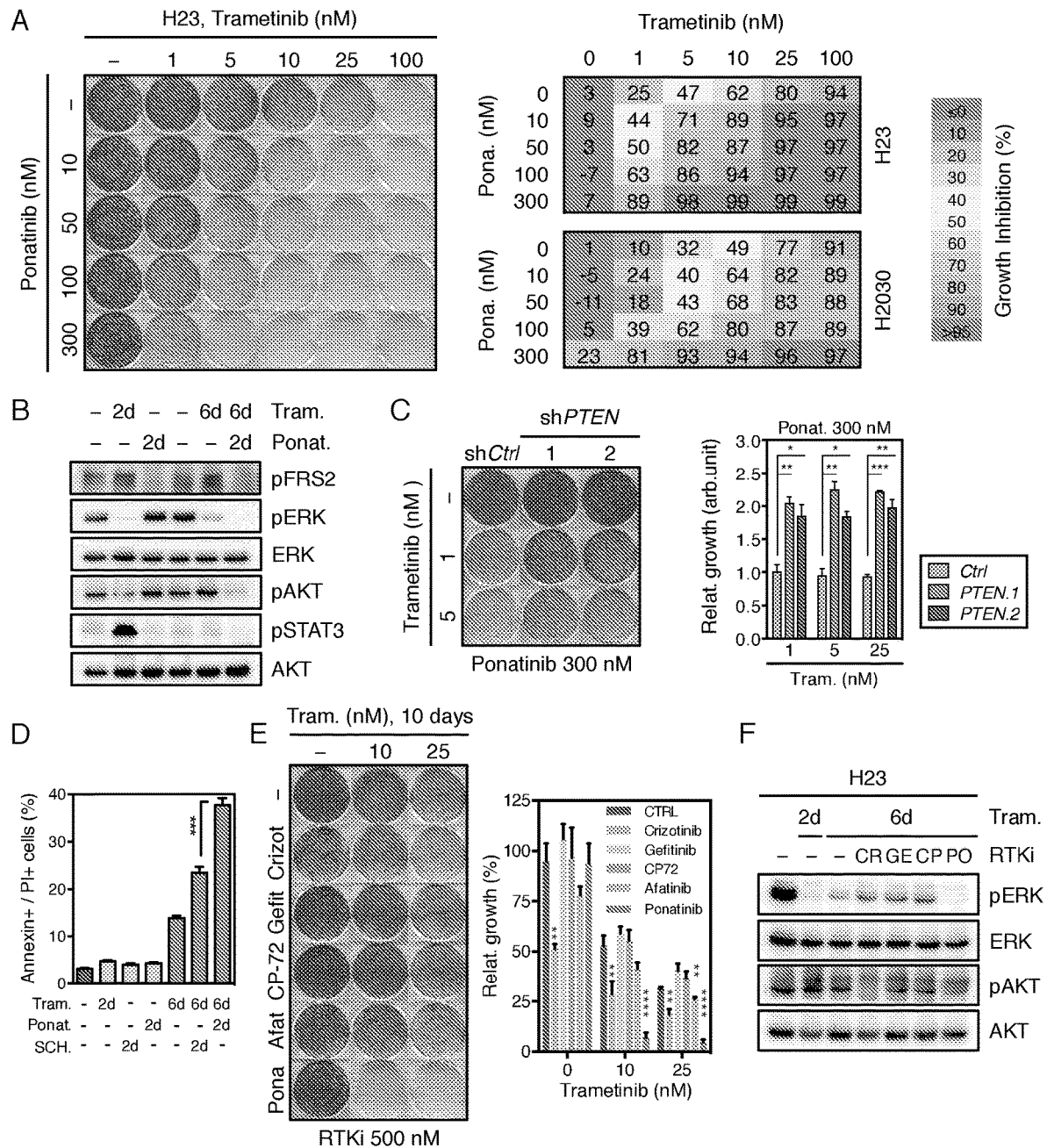
FIG. 19. further documents pharmacological inhibition of FGFR1 enhances the antitumor effect of trametinib leading to tumor cell death. a, Clonogenic assay of H23 cells treated with increasing concentrations of trametinib, ponatinib, or their combination as indicated. A representative example of three independent experiments is shown. Percent inhibition at each concentration of the drug in H23 and H2030 cells is presented (right). Data presented as mean of three independent replicates. b, H23 cells were treated with trametinib (25 nM), ponatinib (300 nM), or their combination for the times shown. H23 cells were pretreated with trametinib for 4 days, followed by treatment with ponatinib and trametinib for 2 days. Lysates were subject to immunoblot analysis with the indicated antibodies. c, Clonogenic assay of H2030 cells transduced with PTEN and non targeting control shRNAs. Cells were treated with ponatinib alone (300 nM) or in combination with trametinib (1 and 5 nM) for 10 days. Quantification of relative growth is shown (right). Error bars represent mean±s.d. *P<0.05, P<0.01, *P<0.001 (n=3). d, AnnexinV/PI double staining assay of H23 cells treated with trametinib (25 nM), ponatinib (300 nM), SCH772984 (1 μM) or their combination for the times shown. Quantification of AnnexinV/PI double positive cells (dead cells) is shown. Error bars represent mean±s.d. *P<0.001 (n=3). e, Clonogenic assay of H23 cells treated with increasing concentration of trametinib alone or in combination with 500 nM crizotinib, gefitinib, CP-724714, afatinib, or 300 nM ponatinib. A representative example of three independent experiments is shown. Quantification of relative growth is presented (right). Data presented as mean of three independent experiments±s.d. P<0.01, ****P<0.0001. f, H23 cells were treated with trametinib (25 nM) alone or in combination with crizotinib (1 μM), gefitinib (1 μM), CP-724714 (1 μM) and ponatinib (300 nM) as indicated. Cells were pretreated with trametinib for 4 days, followed by treatment with other RTK inhibitors and trametinib for 2 days. Lysates were subject to immunoblot analysis with the indicated antibodies.
Figure 26:
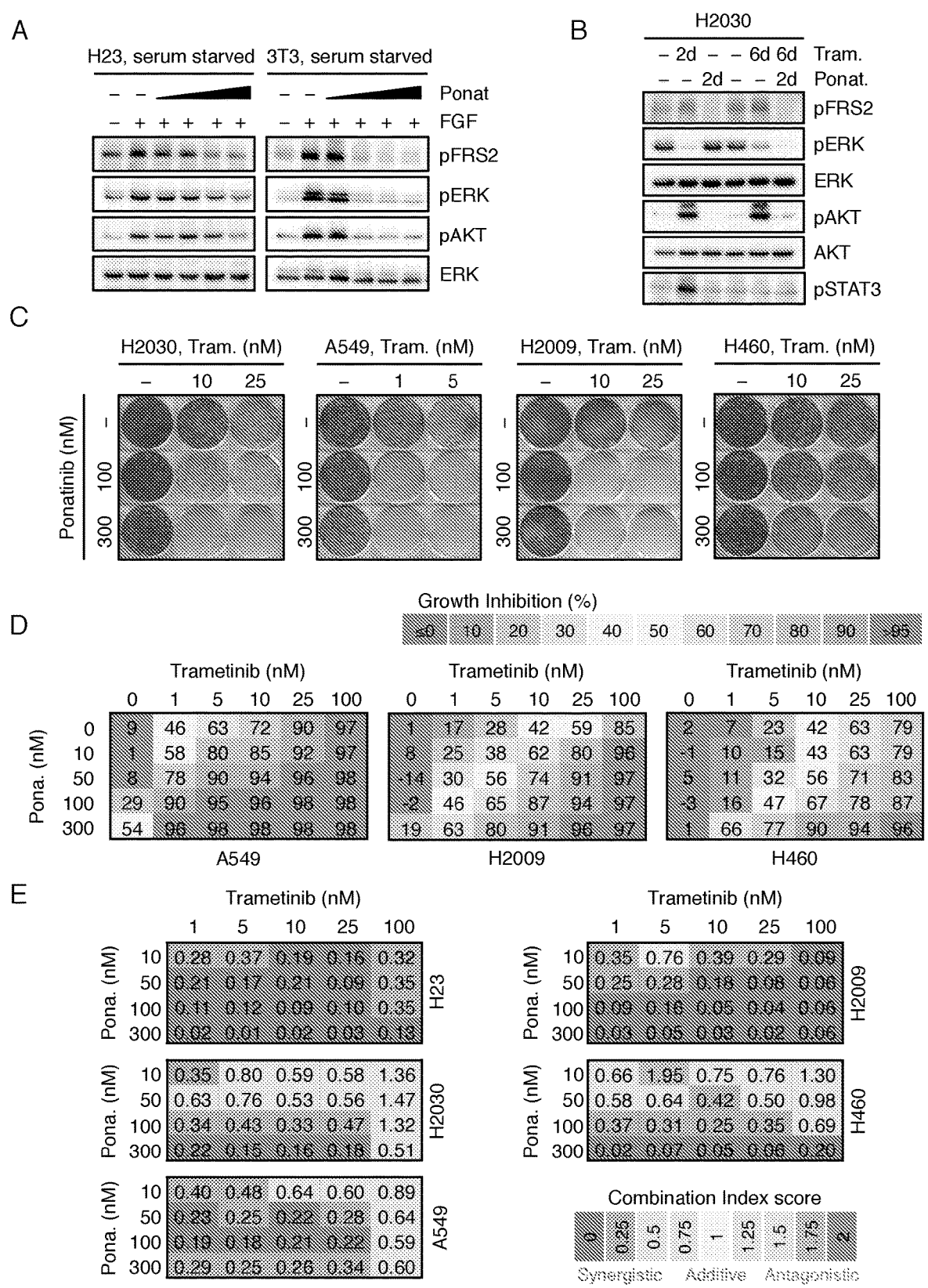
FIG. 26. documents suppression of FGFR1 synergizing with MEK inhibition to promote regression of KRAS-mutant lung cancer cells. a, Serum starved H23 (left panel) and 3T3 (right panel) cells were pre-treated with increasing concentration of ponatinib for 24 hr (1, 30, 100, and 300 nM), followed by stimulation with FGF2 (50 ng/ml) for 10 min. Lysates were subject to immunoblot analysis with the indicated antibodies. b, H2030 cells were treated with trametinib (25 nM), ponatinib (300 nM), or their combination for the times shown. H2030 cells were pretreated with trametinib for 4 days, followed by co-treatment with ponatinib and trametinib for 2 days. Lysates were subject to immunoblot analysis with the indicated antibodies. c, Clonogenic assay of H2030, A549, H2009, and H460 cells treated with increasing concentrations of trametinib, ponatinib, or their combination as indicated. A representative example of three independent experiments is shown. d, Percentage of cell growth inhibition at each concentration of trametinib, ponatinib, or their combination in A549, H2009, and H460 cells after 10 days of treatment. Data presented as mean of three independent experiments. e, Combination Index (CI) scores for H23, H2030, A549, H2009, and H460 cells treated with trametinib in combination with ponatinib at the indicated concentrations. CI scores were calculated using the Chou-Talalay method and categorized as synergistic (<0.75, green), additive (0.75-1.5, blue), or antagonistic (>1.5, red). Each CI score represents data from at least three independent experiments.
Figure 27:
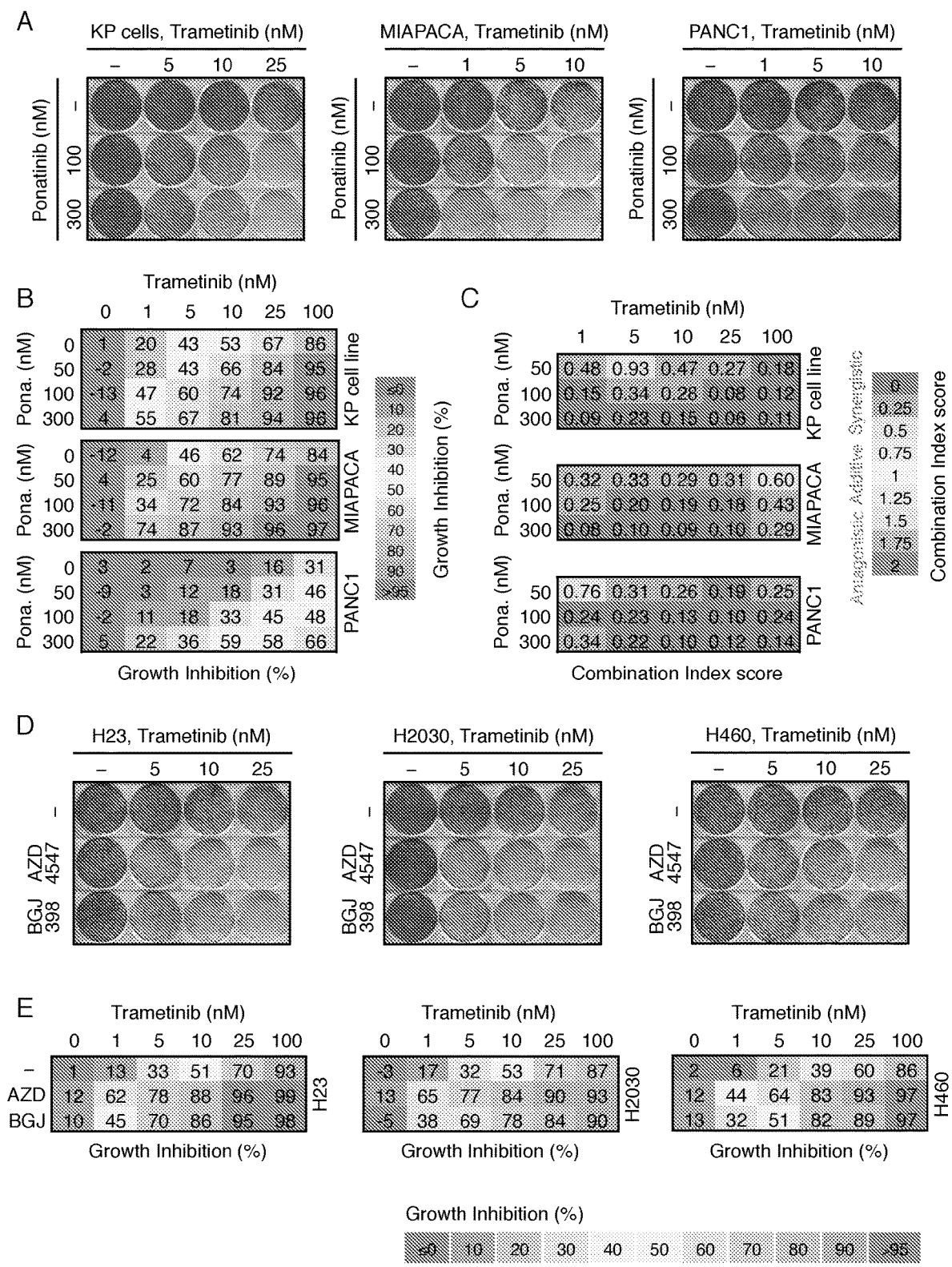
FIG. 27. further documents that FGFR1 inhibitors sensitize murine and human KRAS mutant cancer cells to trametinib. a, Clonogenic assay of a murine lung cancer cell line harboring $Kras^{G12D}$ and $Trp53^{R270H}$ mutations (KP cell line), and human KRAS-mutant pancreatic cancer cell lines (MIAPACA and PANC1). Tumor cells were cultured with increasing concentrations of trametinib, ponatinib, or their combination as indicated. A representative example of three independent experiments is shown. b, Percentage of cell growth inhibition at each concentration of trametinib, ponatinib, or their combination in KP, MIAPACA, and PANC1 cells after 10 days of treatment. Data presented as mean of three independent replicates. c, Combination Index (CI) scores for KP, MIAPACA, and PANC1 cells treated with trametinib in combination with ponatinib at the indicated concentrations. CI scores were calculated using the Chou-Talalay method and categorized as synergistic (<0.75, green), additive (0.75-1.5, blue), or antagonistic (>1.5, red). Each CI score represents data from at least three independent experiments. d, Clonogenic assay of H23, H2030, and H460 cells cultured with increasing concentrations of trametinib alone or in combination with FGFR1 inhibitors BGJ398 (1.5 µM) or AZD4547 (2 µM). A representative example of three independent experiments is shown. e., Percentage of cell growth inhibition at each concentration of trametinib alone or in combination with BGJ398 (1.5 µM) or AZD4547 (2 µM) in H23, H2030, and H460 cells after 10 days of treatment. Data presented as mean of three independent replicates.

We investigated the effect of pharmacologic inhibition of FGFR1 in KRAS-mutant lung cancer. To this end, we decided to use FDA-approved ponatinib, a multikinase inhibitor that potently inhibits FGFR1 and has been in clinical development for the treatment of FGFR1-amplified lung cancers. Inhibition of FGFR1 by ponatinib significantly reduced the phosphorylation of FRS2, ERK, and AKT in FGF2-treated H23 cells (FIG. 11b, FIG. 26a). While ponatinib alone did not affect the viability of tumor cells, cotreatment of ponatinib and Trametinib resulted in a strong synergistic interaction in multiple KRAS-mutant lung cancer cell lines (FIG. 3f FIG. 11b, c, FIG. 19 a,b). Ponatinib, in combination with Trametinib, showed similar efficacy at a lower dose and in a murine lung tumor cell line harboring point mutations in KRAS and p53 (FIGS. 11d and 12). Further confirming our results, we observed comparable effects using the small molecules BGJ398 and AZD4547, two selective FGFR inhibitors for FGFR1/2/3 with weak activity against FGFR4 and other RTKs (FIG. 13, FIG. 27 d,e). Together with our genetic studies using FGFR1 shRNAs, these results indicate that pharmacological inhibition of FGFR1 can synergize with MEK inhibition in KRAS-mutant lung cancer.

Figure 14:
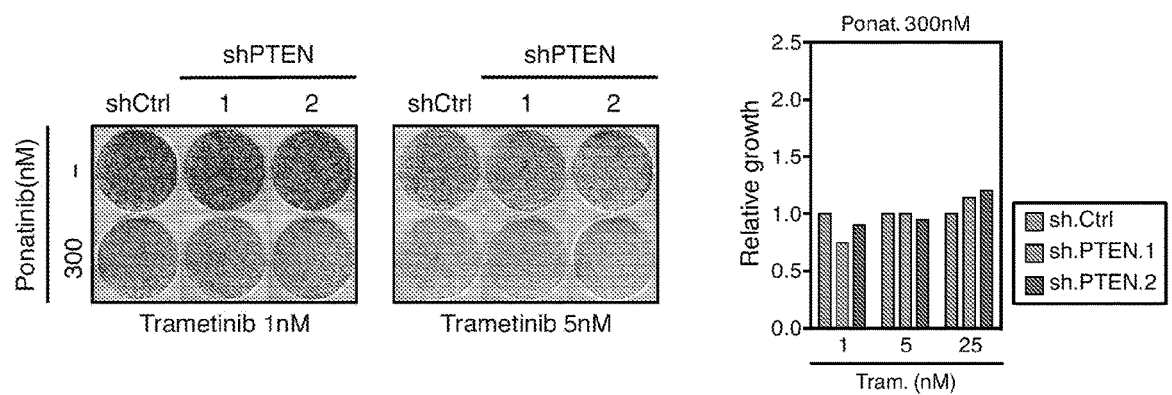
FIG. 14 shows FGFR1 inhibition efficiently inhibits reactivation of MAPK and PI3K signaling following MEK inhibition. a, Clonogenic assay of H460 cells transduced with PTEN and non-targeting control shRNAs. Cells were treated with trametinib (1 and 5 nM) alone or in combination with ponatinib (300 nM) for 10 days, and remaining cells were fixed, stained with crystal violet, and photographed. Relative cell growth was quantified by densitometry after extracting crystal violet from the stained cells using 10% of acetic acid. A representative example of three independent experiments is shown. b, c, H2030 transduced with PTEN and non-targeting control shRNAs were treated with trametinib (25 nM) alone or in combination with ponatinib (300 nM) for the times shown. Changes in phosphorylation of ERK and AKT were determined by immunoblot.
Figure 14:
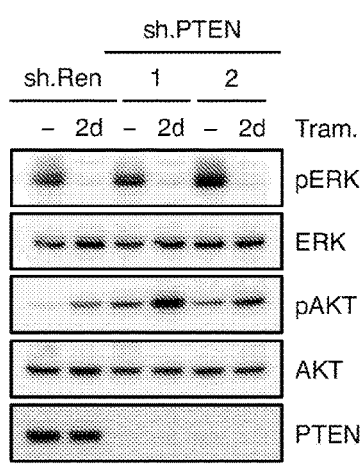
Figure 14:
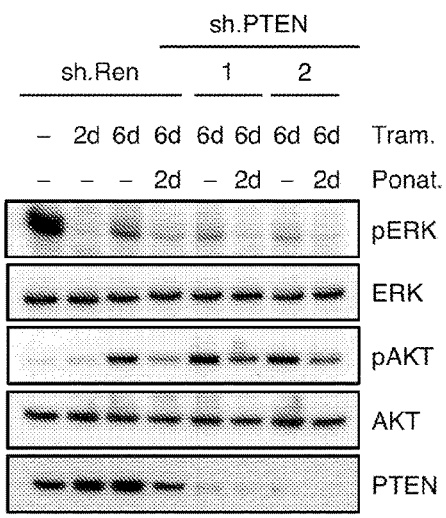
Figure 15:
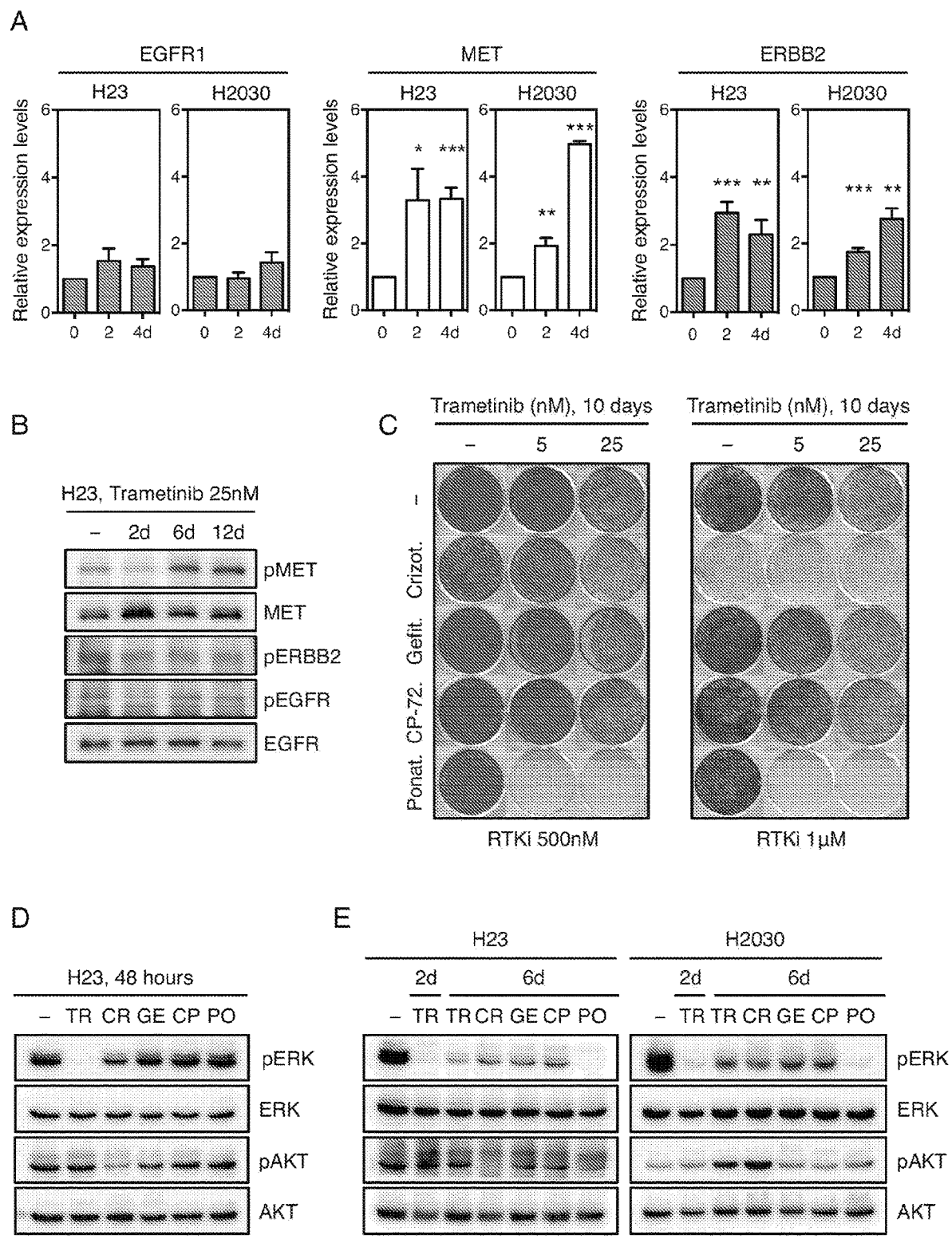
FIG. 15 shows unresponsiveness of KRAS-mutant lung cancer cells to MEK inhibition is specifically mediated by FGFR1 activation. a, qRT-PCR for EGFR, MET, and ERBB2 in H23 and H2030 cells treated with trametinib for the indicated times. Data presented as mean normalized EGFR, MET, and ERBB2 expression±SD. *p<0.05, p<0.01, *p<0.001. b, H23 cells were treated with 25 nM of trametinib for 2, 6, and 12 days. Levels of pMET, pERBB2, and pEGFR were determined by immunoblot. c, Clonogenic assay of H23 cells treated with increasing concentration of trametinib alone or in combination with 500 nM or 1 µM of crizotinib, gefitinib, CP-724714, or 300 nM of ponatinib. Cells were fixed, stained with crystal violet, and photographed. d, e, H23 and H2030 were treated with trametinib (25 nM), crizotinib (500 nM), gefitinib (500 nM), CP-724714 (500 nM), ponatinib (300 nM), or their combination for the times shown. Cells were pretreated with trametinib for 4 days, followed by treatment with other RTK inhibitors for 2 days. Lysates were subjected to immunoblot analysis with the indicated antibodies.
Figure 16:
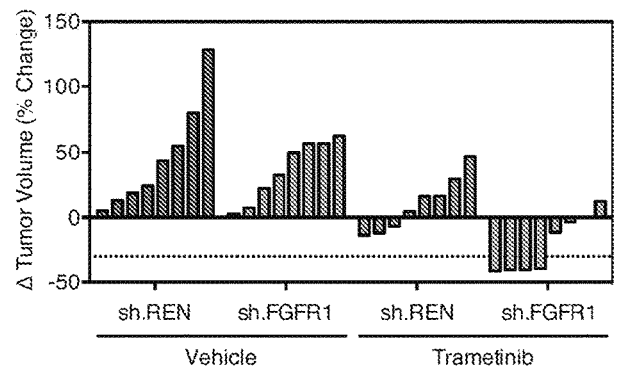
FIG. 16. Shows inhibition of FGFR1 synergizes with trametinib to suppress growth of KRAS-mutant lung cancer in vivo. a, Mice bearing H23 xenografts transduced with FGFR1 or non-targeting control shRNAs were treated daily with either vehicle or trametinib (3 mg/kg) for 5 weeks. A waterfall representation of the best response for each tumor is shown. c, Body weight of mice bearing A549 xenografts with the indicated drug treatment was measured periodically during 5 weeks. Error bars represent mean±SEM. d, Images of explanted A549 subcutaneous tumors following 5 weeks of treatment with the indicated drug regimens.
Figure 16:
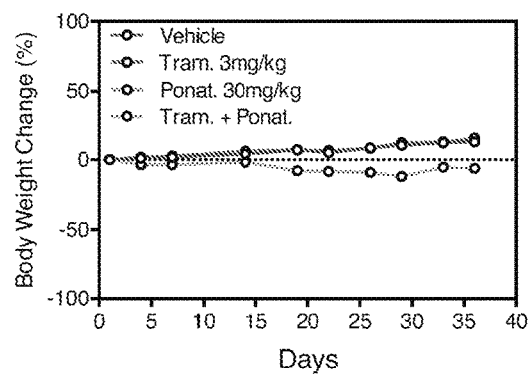
Figure 16:
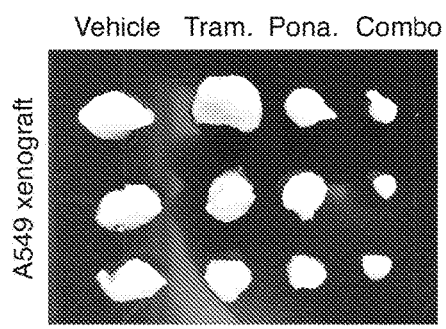

To address the mechanism underlying the synergy between FGFR1 and MEK inhibition, we tested phospholevels of ERK and AKT in lysates of drug-treated cells. Whereas ponatinib alone did not affect the levels of pERK, suggesting that FGFR1 is not required for ERK signaling in KRAS-mutant cells, FGFR1 inhibition prevented feedback activation of ERK and AKT signaling following MEK inhibition (FIG. 3g and FIG. 14). Without wishing to be bound by any particular theory, we hypothesized that inhibition of the rebound in AKT signaling contributes to the effectiveness of FGFR1 inhibition when combined with Trametinib. Indeed, knockdown of PTEN partially rescued the viability of H2030 cells treated with the combination drug regimen as compared to cells transduced with a non-targeting control shRNA (FIG. 3h, 19c). Consistently, suppression of PTEN in H460 cells, a cell line that harbors an activating mutation in the p110α catalytic subunit of PI3K, did not reduce the antitumor effects of the drug combination (FIG. 15). Mechanistically, PTEN inactivation did not impact ERK signaling or its inhibition by treatment with Trametinib. However, PTEN knockdown increased the basal activation of AKT signaling, and more importantly, limited the effect of ponatinib to inhibit the feedback activation of AKT signaling following MEK inhibition (FIG. 15b, c). In agreement with the role of AKT signaling in cell survival, co-treatment of H23 cells with trametinib and ponatinib resulted in higher levels of cell death as compared to monotherapy with trametinib or when combined with the ERK inhibitor SCH772984 (FIG. 19d and FIG. 28d). Together, these findings indicate that ponatinib specifically disrupts feedback reactivation of MAPK and PI3K signaling that, in combination, produces adaptive resistance in KRAS-mutant lung cancer.

Figure 28:
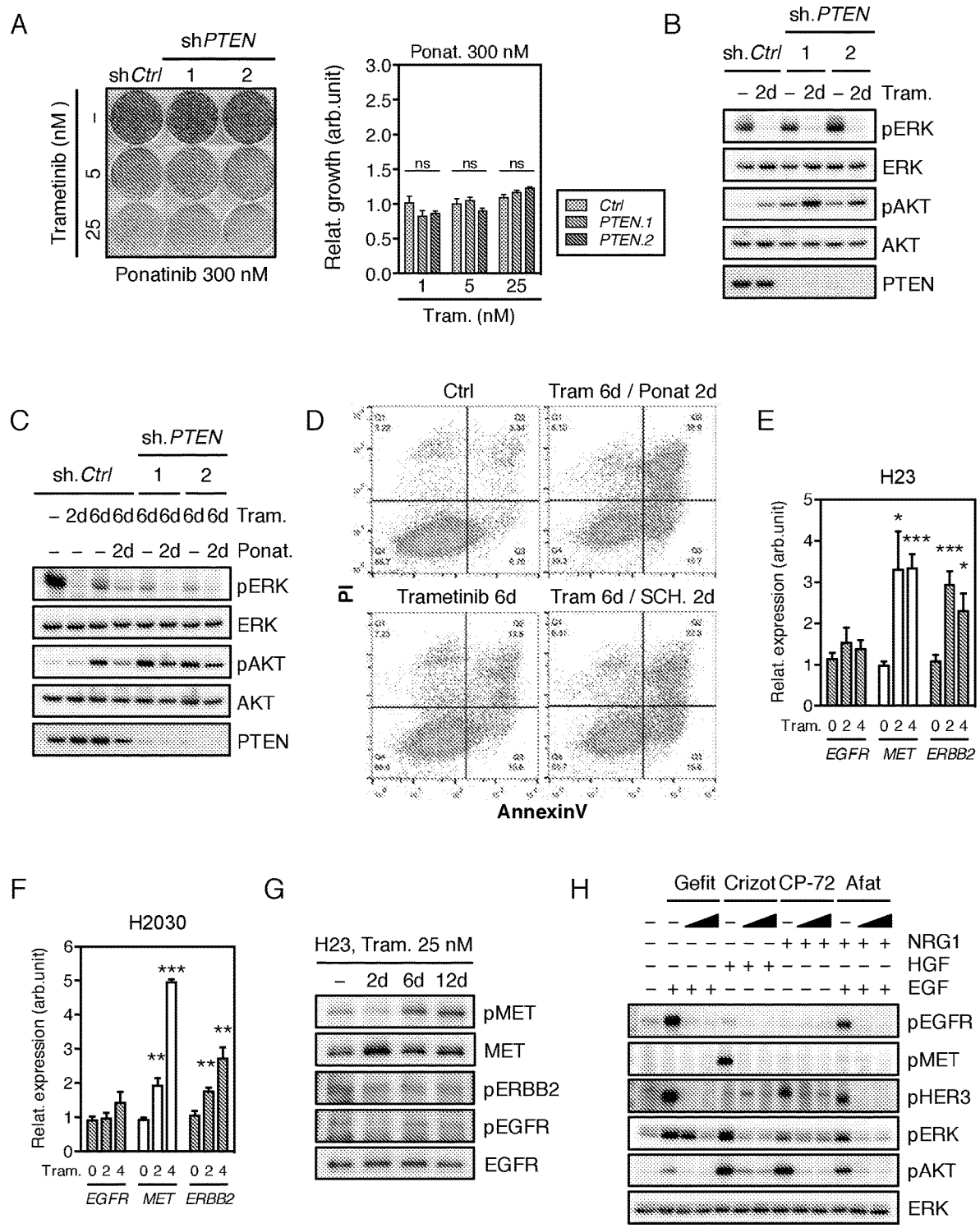
FIG. 28. Further documents that ponatinib inhibits trametinib-induced reactivation of MAPK and PI3K signaling. Upregulation of distinct RTKs in KRAS-mutant lung cancer cells after trametinib treatment. a, Clonogenic assay of H460 cells transduced with PTEN and non targeting control shRNAs. Cells were treated with ponatinib alone (300 nM) or in combination with trametinib (5 and 25 nM) for 10 days. Quantification of the relative cell growth is shown (right). Error bars represent mean±s-.d. (n=3). b, c, H2030 transduced with PTEN and non targeting control shRNAs were treated with trametinib (25 nM) alone (b) or in combination with ponatinib (300 nM) (c) for the times shown. Changes in phosphorylation of ERK and AKT were determined by immunoblot. d, AnnexinV/PI double staining assay of H23 cells treated with vehicle, trametinib (25 nM) alone, or in combination with ponatinib (300 nM) or SCH772984 (1 µM) for the times shown. A representative example of three independent experiments is shown. e, f, qRT-PCR for EGFR, MET, and ERBB2 in H23 (e) and H2030 (f) cells treated with trametinib for 0, 2, and 4 days. Data presented as mean normalized for EGFR, MET, and ERBB2 expression±s.d. *P<0.05, P<0.01, *P<0.001. g, H23 cells were treated with 25 nM of trametinib for various times. Levels of pMET, pERBB2, and pEGFR were determined by immunoblot. h, Serum starved H2030 cells were pre-treated with 500 nM or 1 µM of gefitinib, crizotinib, CP-724714, or afatinib for 12 hr, followed by stimulation with EGF, HGF, NRG1, or their combination (50 ng/ml) for 10 min. Lysates were subject to immunoblot analysis with the indicated antibodies.
Figure 29:
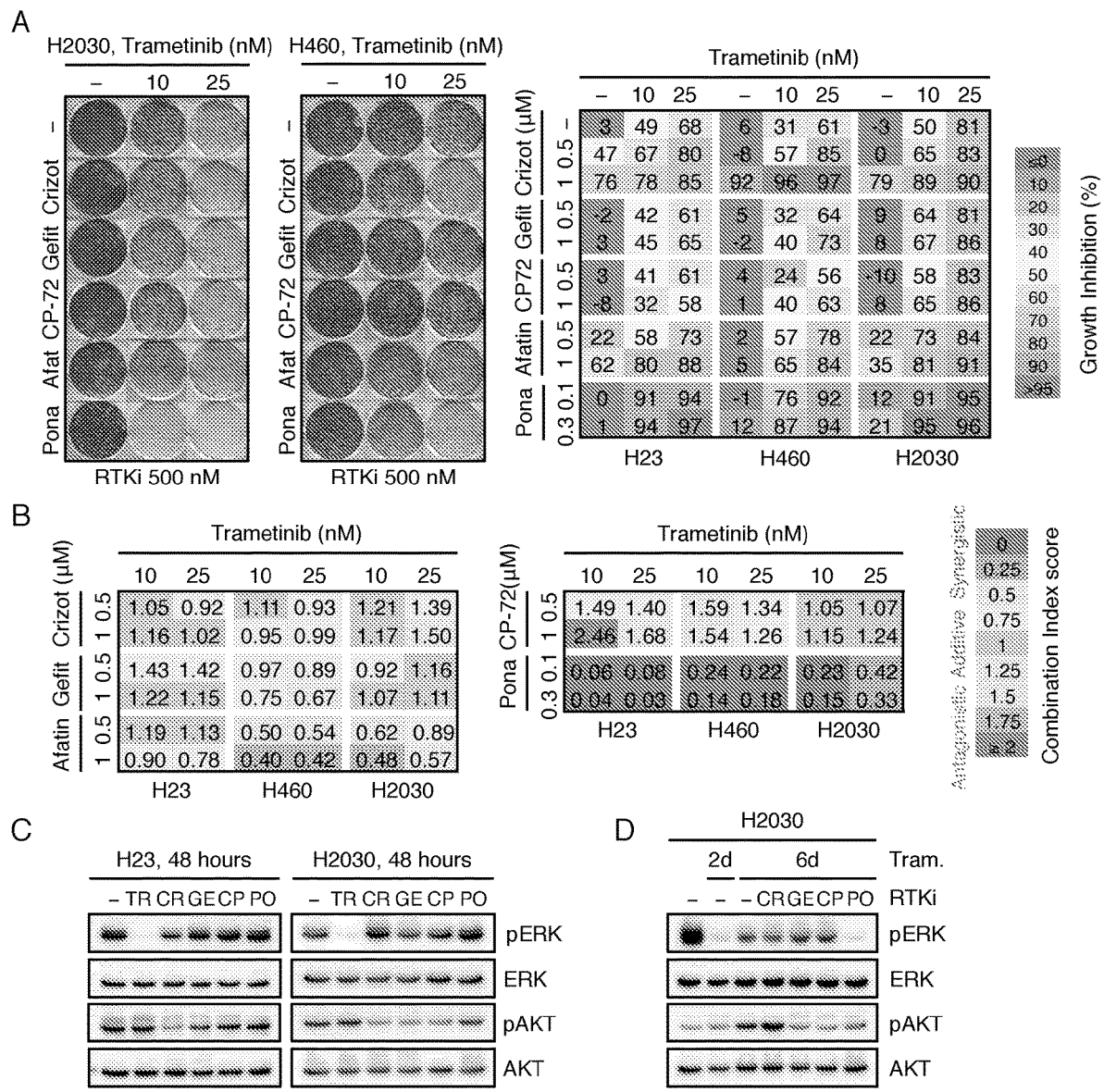
FIG. 29. Further documents that unresponsiveness of KRAS-mutant lung cancer cells to MEK inhibitor trametinib is specifically mediated by feedback activation of FGFR1 signaling. a, Clonogenic assay of H2030 and H460 cells treated with increasing concentration of trametinib alone or in combination with 500 nM crizotinib, gefitinib, CP-724714, afatinib, or 300 nM ponatinib. A representative example of three independent experiments is shown. Percent inhibition at each concentration of the drug in H23, H460, and H2030 cells is presented (right). Data presented as mean of three independent experiments. b, Combination Index (CI) scores for H23, H460, and H23 cells treated with trametinib in combination with crizotinib, gefitinib, CP-724714, afatinib, and ponatinib at the indicated concentrations. CI scores were calculated using the Chou-Talalay method and categorized as synergistic (<0.75, green), additive (0.75-1.5, blue), or antagonistic (>1.5, red). Each CI score represents data from at least three independent experiments. c, H23 and H2030 were treated with trametinib (25 nM), crizotinib (1 µM), gefitinib (1 µM), CP-724714 (1 µM), and ponatinib (300 nM) for 48 hours. Lysates were subject to immunoblot analysis with the indicated antibodies. d, H2030 were treated with trametinib (25 nM), crizotinib (1 µM), gefitinib (1 µM), CP-724714 (1 µM), ponatinib (300 nM), or their combination for the times shown. Cells were pretreated with trametinib for 4 days, followed by co-treatment with RTK inhibitors and trametinib for 2 days. Lysates were subject to immunoblot analysis with the indicated antibodies.

To further investigate the specificity of FGFR1 in promoting Trametinib-resistance in KRAS-mutant lung cancer, we explored whether other specific RTKs might mediate the same response. MEK inhibition led to upregulation of MET and ERBB2, but not EGFR, and correlated with activation of MET signaling (FIG. 28). However, no synergy was observed in H23 cells when crizotinib, CP724714, and gefitinib, targeting MET, ERBB2, and EGFR, respectively, were combined with Trametinib. Providing a rationale for these results, we observed that selective inhibition of these RTKs did not prevent the rebound in ERK signaling following MEK inhibition (FIG. 28h). Consistent with previous reports, the dual EGFR/ERBB2 inhibitor afatinib enhanced trametinib activity in some KRAS-mutant lung cancer cell lines, but the efficacy and synergy of this combination was weaker than the trametinib and ponatinib combination (FIG. 19e and FIG. 29a, b). Accordingly, none of these drugs prevented the rebound in ERK signaling following trametinib treatment (FIG. 19f and FIG. 29c, d). These results suggest that feedback activation of FGFR1 signaling is a prominent mechanism of adaptive resistance to the MEK inhibitor trametinib in KRAS-mutant lung cancer.

Figure 4:
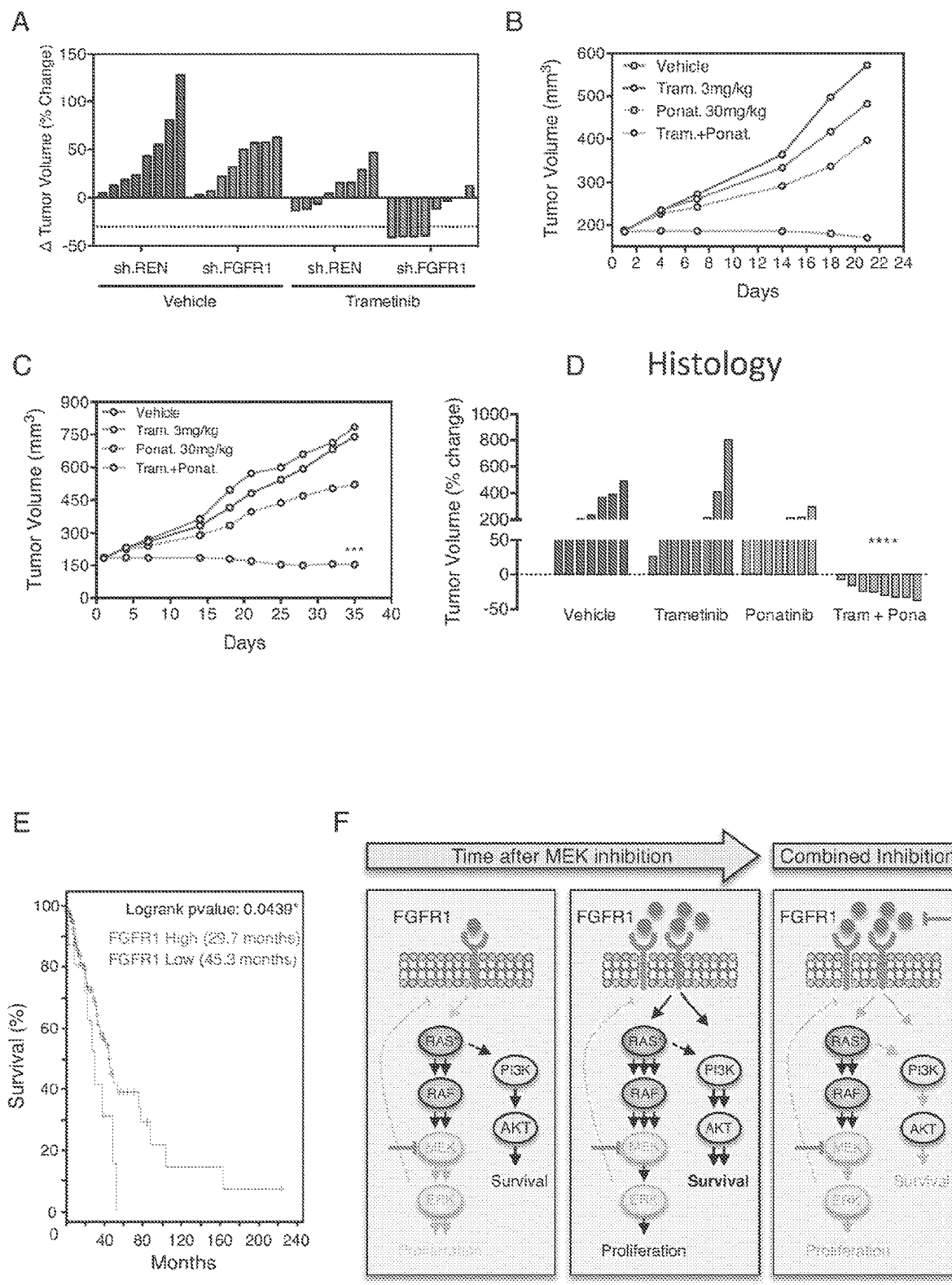
FIG. 4. shows suppression of FGFR1 synergizes with MEK inhibition to promote regression of KRAS-mutant lung tumors in vivo. a, b, Mice bearing A549 xenografts were treated daily with either vehicle or trametinib (3 mg/kg) for 5 weeks. The tumors volumes are shown as a function of time after treatment. Error bars represent mean±SEM. *p<0.0005 (a). A waterfall representation of the best response for each tumor is shown. **p<0.0001. c, Tumor tissue from A549 xenografts treated for 3 or 12 days as indicated was evaluated by IHC for phospho-ERK and phospho-AKT. Tumors were harvested 4 hours after dosing on day 3 or 12. d, e, Mice bearing LX55a patient derived xenografts were treated daily with vehicle, trametinib (3 mg/kg), ponatinib (30 mg/kg), or both drugs in combination for 13 days. The tumors volumes are shown as a function of time after treatment. Error bars represent mean±SEM (d). A waterfall representation of the best response for each tumor is shown (e).
Figure 5:
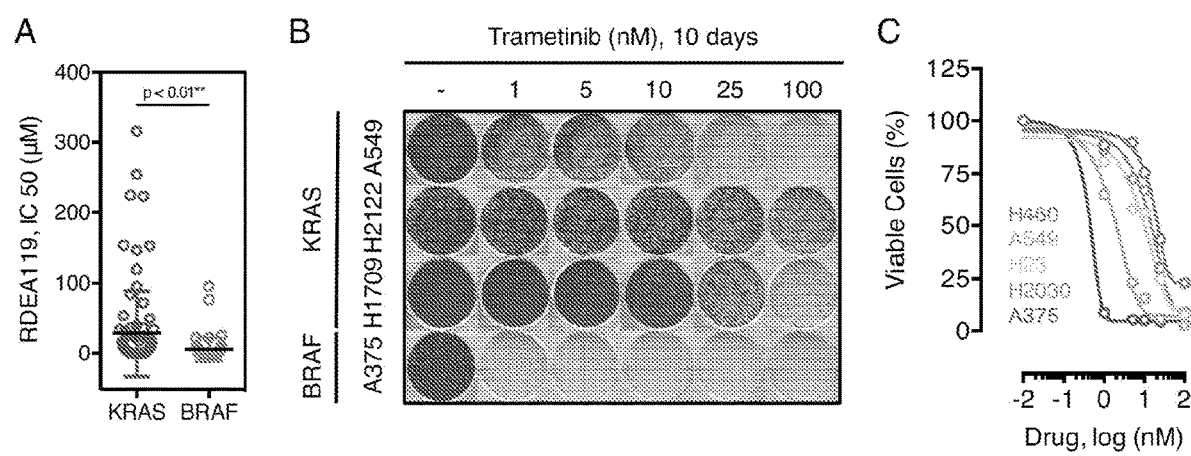
FIG. 5 shows KRAS-mutant tumors are less sensitive to MEK inhibition than BRAF-mutant tumors. a, The Genomic of Drug Sensitivity in Cancer dataset was analyzed to determine if sensitivity to MEK inhibitor RDEA119 correlates with tumor genotype. The IC50 of RDEA119 in KRAS- and BRAF-mutant cell lines is shown. **p<0.01. b, Clonogenic assay of KRAS-(A549, H2122, H1709) and BRAF-mutant lung cancer cell lines. Cells were cultured in the absence or presence of trametinib at the indicated concentrations for 10 days. Remaining cells were fixed, stained with crystal violet, and representative dishes are shown. c, Cell viability of of KRAS-(H460, A549, H23, and H2030) and BRAF-mutant (A375) lung cancer cell lines treated with increasing doses of trametinib for 10 days.
Figure 30:
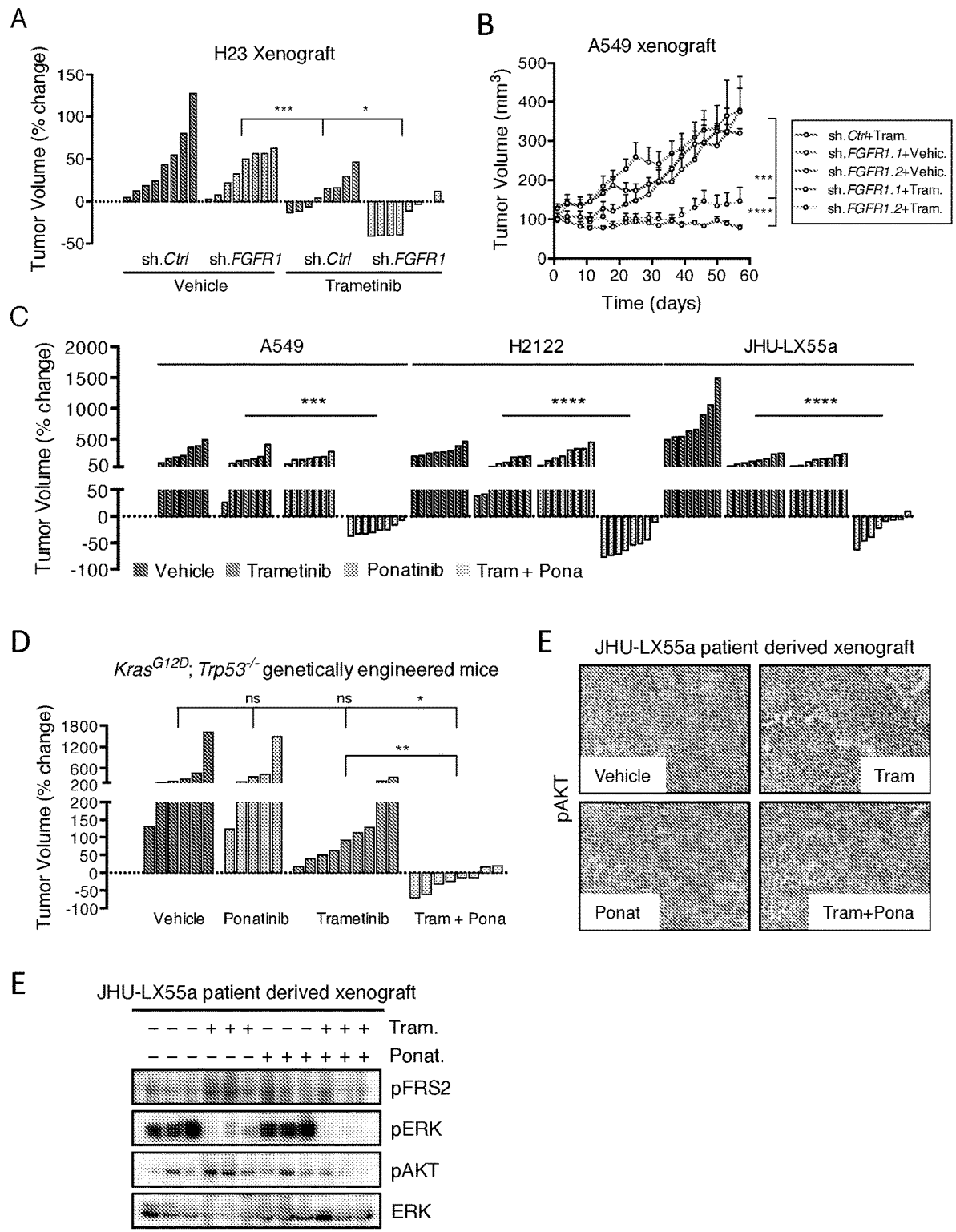
FIG. 30. Further documents that suppression of FGFR1 synergizes with trametinib to inhibit growth in vivo of KRAS-mutant lung tumors. a, b, Mice bearing H23 (a) or H2030 (b) xenografts transduced with FGFR1 or non-targeting control shRNAs were treated with either vehicle or trametinib (3 mg/kg). For H23 xenografts, a waterfall representation of the best response for each tumor is shown (a) *P<0.05, *P<0.001. For H2030 xenografts, the tumor volumes are shown as a function of time after treatment (b). Error bars represent mean±s.e.m. *P<0.001, **P<0.0001. c, Mice bearing A549 and H2122 xenografts, and JHU-LX55a patient-derived xenograft tumors were treated with vehicle, trametinib (3 mg/kg), ponatinib (30 mg/kg), or both drugs in combination. A waterfall representation of the best response for each tumor is shown. *P<0.001, ****P<0.0001. d, $Kras^{G12D}$; $Trp53^{-/-}$ genetically engineered mice harboring lung adenocarcinomas were treated with vehicle, trametinib (3 mg/kg), ponatinib (30 mg/kg), or both drugs in combination for 7 weeks. A waterfall representation of the response for each tumor after 7 weeks of treatment is shown. ns: not significant, *P<0.05, **P<0.01. e, Tumor tissue from JHU-LX55a patient derived xenografts treated with vehicle, trametinib (3 mg/kg), ponatinib (30 mg/kg), or both drugs in combination for 18 days was evaluated by IHC for phospho-AKT. Tumors were harvested 4 hours after dosing on day 18. f, Tumor tissue from mice bearing JHU-LX55a patient-derived xenografts treated with vehicle, trametinib (3 mg/kg), ponatinib (30 mg/kg), or both drugs in combination for 18 days was subject to immunoblot analysis with the indicated antibodies.

We also tested the effectiveness of combining FGFR1 and MEK inhibition in vivo by using KRAS-mutant lung cancer xenografts. To this end, A549 and H23 xenografts harboring tet-responsive FGFR1 or non-targeting control shRNAs were treated with doxycycline and a daily dose of 3 mg/kg of Trametinib when tumors reached 150 mm$^3$. Relative to vehicle-treated controls, treatment with Trametinib alone led to only a modest inhibition of tumor growth in H23 xenografts and no significant tumor inhibition in A549 xenografts. However, the combination of FGFR1 knockdown with Trametinib led to potent tumor inhibition and caused tumor regression in most tumors (FIG. 4a, b and FIG. 30).

Figure 20:
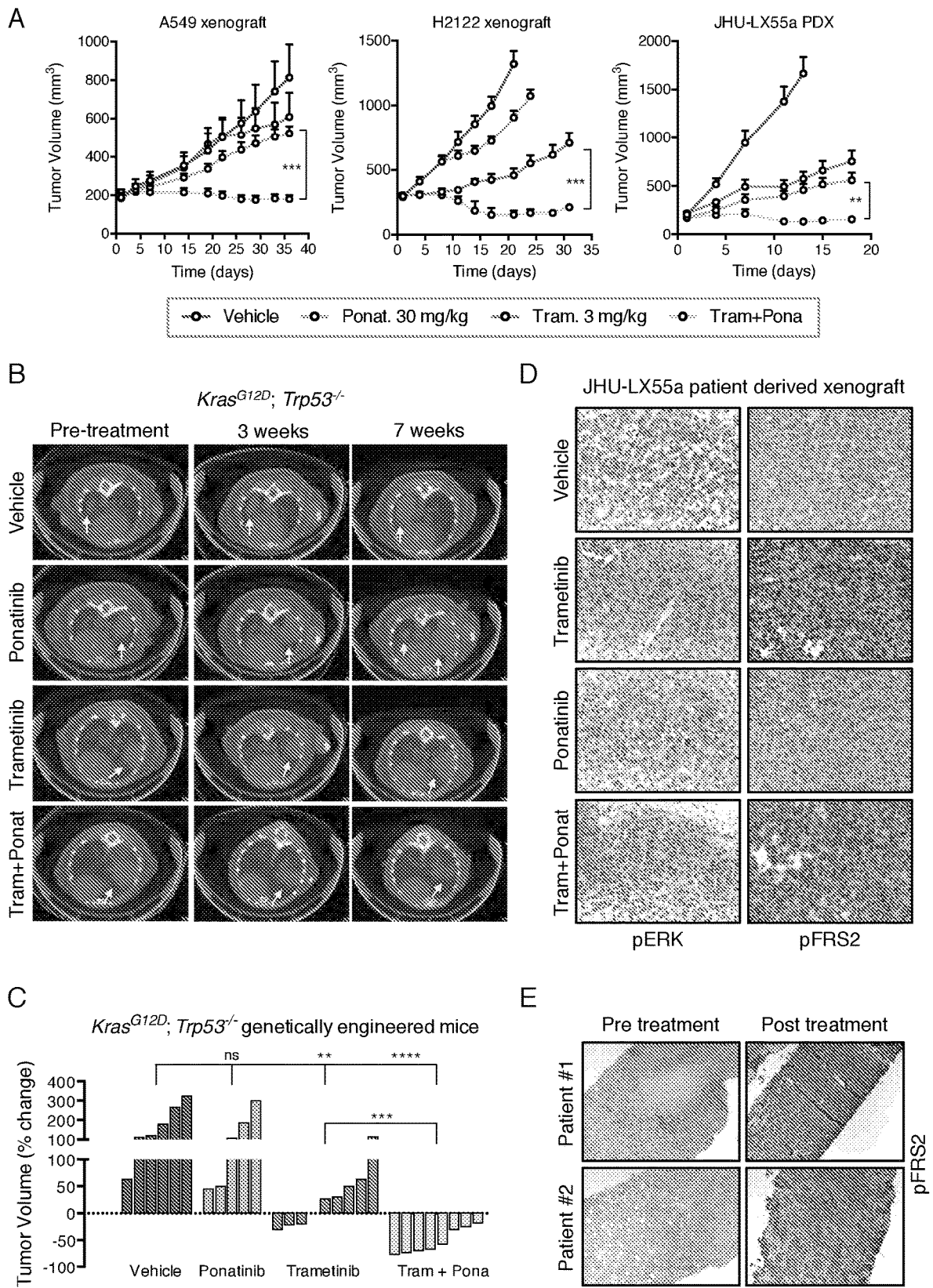
FIG. 20. Further documents that suppression of FGFR1 synergizes with trametinib to promote regression of KRAS-mutant lung tumors in vivo. a, Mice bearing A549 and H2122 xenografts, and JHU660 LX55a patient-derived xenograft tumors were treated with vehicle, trametinib (3 mg/kg), ponatinib (30 mg/kg), or both drugs in combination for the indicated times. The tumor volumes are shown as a function of time after treatment. Error bars represent mean±s.e.m. *P<0.001, P<0.01. b, c, Representative μCT images of the lungs of $Kras^{G12D}$; $Trp^{53-/-}$ genetically engineered mice treated with vehicle, trametinib (3 mg/kg), ponatinib (30 mg/kg), or both drugs in combination for 3 and 7 weeks. Lung tumors are indicated by yellow arrows and red asterisks mark the hearts (b). A waterfall representation of the response for each tumor after three weeks of treatment is shown (c). ns: not significant, P<0.01, *P<0.001, ****P<0.0001. d, Tumor tissue from JHU-LX55a patient derived xenografts treated with vehicle, trametinib (3 mg/kg), ponatinib (30 mg/kg), or both drugs in combination for 18 days was evaluated by IHC for phospho-ERK and phospho-FRS2. Tumors were harvested 4 hours after dosing on day 18. e, Paired tumor biopsies from patients having KRAS-mutant lung adenocarcinomas (before and after treatment with the MEK inhibitor trametinib) were evaluated by IHC for phospho-FRS2. Patients #1 and #2 were treated with trametinib for 16 and 22 days, respectively.

We examined the efficacy of combining ponatinib and Trametinib in A549 and H2122 xenograft models. When tumors reached 150-200 mm$^3$, vehicle, Trametinib, ponatinib, or the drug combination was orally administered at an effective dose. Each inhibitor alone resulted in marginal growth inhibition, with no regression observed in any tumor. In contrast, combination of ponatinib and Trametinib provoked regression of all tumors (FIG. 4c, d and FIG. 30). Notably, comparable results were observed in a KRAS-mutant patient derived xenograft model of lung cancer, where the combination of FGFR1 and MEK inhibition was superior to either drug alone (FIG. 4e, f). Consistent with our in vitro results, trametinib treatment led to activation of FGFR1 signaling, as indicated by an increase in the levels of pFRS2, and consequently induction of ERK and AKT signaling, which was prevented by ponatinib (FIG. 20d and FIG. 30e, f). These studies provide strong support for combined MEK and FGFR1 inhibition in KRAS-mutant lung cancer, and suggest that tumors capable of reactivating FGFR1 signaling will be most sensitive to this combinatorial strategy. Taken together, these results suggest that combined inhibition of FGFR1 and MEK has enhanced antitumor activity and that this is due to more complete inhibition of ERK and AKT signaling.

To evaluate the clinical relevance of our findings, we assessed the FRS2 phosphorylation in tumor biopsies before and after trametinib treatment from two patients with KRAS-mutant lung adenocarcinoma. In both cases, a pronounced increase in pFRS2 levels was observed in the post-treatment biopsies (FIG. 20e). These results demonstrate that trametinib provokes FGFR1 activation in KRAS-mutant human tumors and pinpoint a potential biomarker that might eventually be used to identify patients likely to benefit from this drug combination.

Using a non-biased screening approach, this study has shown that reactivation of ERK signaling represents a mechanism that limits the overall response of KRAS-mutant lung tumors to MEK inhibition. Prevention of ERK signaling rebound by genetic or pharmacologic means enhanced the antitumor properties of MEK inhibition, highlighting the predominance of MAPK signaling in these tumors. The strong feedback activation of FGFR1 elicited by MEK inhibition explains the strong synergistic effect observed between FGFR1 and MEK inhibition, and provides a rational for the poor clinical response of KRAS-mutant lung cancer to Trametinib. This effect was specific: although induction of other RTKs was observed in trametinib-treated KRAS-mutant lung cancer cells, only shRNAs targeting FGFR1, but not other FGFR family members or other RTKs, conferred sensitivity to trametinib, and only inhibition of FGFR1 blocked the reactivation of both ERK and AKT. Consistent with this, an unbiased ORF screen for identifying genes able to overcome KRAS addiction identified FGFR1, but not other RTKs, as sufficient to allow proliferation in the presence of KRAS suppression. Accordingly, combined use of trametinib and FGFR1 inhibitors, including the FDA-approved drug ponatinib, produced a marked increase in anti-tumor activity leading to tumor regression. Sensitivity to the combination was precisely predicted by FRS2 phosphorylation, which is indicative of FGFR activation; in principle, post treatment biopsies indicating an increase in pFRS2 levels following trametinib treatment would be predictive of success of the combination. Although careful attention to additive or synergistic toxicities will be required for the clinical implementation of these observations, it seems likely that targeting a specific RTK such as FGFR1 will be more tolerable than targeting more pleiotropic factors such as AKT and presents a rationale for developing more specific FGFR1 antagonists. Regardless, our study provides compelling evidence that targeting adaptive resistance mechanisms can improve the efficacy of molecular targeted therapies and suggests a path towards developing rational therapies for KRAS-mutant lung cancer.

Example 2: Experimental Methods

The present Example describes experimental methods used to achieve the preceding results.

Pooled Negative-Selection RNAi Screening

A custom shRNA library targeting the full complement of 526 human kinases was designed using miR30-adapted DSIR predictions refined with "sensor" rules (six shRNAs per gene) and constructed by PCR-cloning a pool of oligonucleotides synthesized on 12k customized arrays (Agilent Technologies and CustomArray) as previously described (Supplementary Table 1). The list of genes was obtained from KinBase Database (http://kinase.com/human/kinome/) and was manually curated. After sequence verification, 3156 shRNAs (5-6 per gene) were combined with 20 positive- and negative-control shRNAs at equal concentrations in one pool. This pool was subcloned into the TRMPV-Neo vector and transduced in triplicates into Tet-on H23 KRAS mutant lung cancer cells using conditions that predominantly lead to a single retroviral integration and represent each shRNA in a calculated number of at least 1,000 cells. Transduced cells were selected for 6 days using 1 mg ml$^{-1}$ G418 (Invitrogen); at each passage more than 30 million cells were maintained to preserve library representation throughout the experiment. After drug selection, T0 samples were obtained (~30 million cells per replicate (n=3)) and cells were subsequently cultured in the presence or absence of trametinib (25 nM) and 1 μg ml$^{-1}$ doxycycline to induce shRNA expression. After ten population doublings (Tf), about fifteen million shRNA-expressing (dsRed+/Venus+260) cells were sorted for each replicate using a FACSAriaII (BD Biosciences). Genomic DNA from T0 and Tf samples was isolated by two rounds of phenol extraction using PhaseLock tubes (5prime) followed by isopropanol precipitation. Deep-sequencing template libraries were generated by PCR amplification of shRNA guide strands as previously described. Libraries were analyzed on an Illumina Genome Analyzer at a final concentration of 8 pM; 50 nucleotides of the guide strand were sequenced using a custom primer (miR30EcoRISeq, (SEQ ID NO.1: TAGCCCCTTGAATTCCGAGGCAGTAGGCA). To provide a sufficient baseline for detecting shRNA depletion in experimental samples, we aimed to acquire >500 reads per shRNA in the T0 sample, which required more than twenty million reads per sample to compensate for disparities in shRNA representation inherent in the pooled plasmid preparation or introduced by PCR biases. With these conditions, we acquired T0 baselines of >500 reads for (97.9%) shRNAs. Sequence processing was performed using a customized Galaxy platform.

Using selection criteria that required an shRNA depletion averaging greater than 4-fold after ten population doublings and an effect greater than 4-fold in trametinib-treated cells with respect to untreated ones, 64 shRNAs were identified. The 8 targets for which at least two shRNAs were selectively depleted following trametinib treatment were subject to secondary validation in cell competition assays using multiple KRAS-mutant lung cancer cell lines. 6 targets validated in the cell line in which the primary screen was performed (H23 cells) and 4 (BRAF, CRAF, ERK2, and FGFR1) across a panel of KRAS-mutant lung cancer cells, and as such these represented the top hits of our screen.

Plasmids and Recombinant Proteins

All vectors were derived from the Murine Stem Cell Virus (MSCV, Clontech) retroviral vector backbone. miR30-based shRNAs were designed and cloned as previously described and sequences are available in Supplementary Table 1. shRNAs were cloned into the TRMPV-Neo (pSIN-TREdsRed-miR30-PGK-Venus-IRES-NeoR) and MLP (LTR-miR30-PGK-PuroR-IRESGFP) vectors as previously described. All constructs were verified by sequencing. Recombinant proteins FGF2 (8910, Cell Signaling), HGF (100-39, Peprotech), EGF (AF-100-15, Peprotech), and NRG1 (100-03, Peprotech) were used at 50 ngml-1 290 for 10 minutes.

Cell Culture, Compounds, and Competitive Proliferation Assays

H23, H460, H2030, H358, H2122, H2009, H1975, H1650, Ludlu-1, H1703, SW480, SW620, and DLD-1 cells were cultured in RPMI media; A549, 3T3, H1299, MIAPACA-2, PANC-1, and murine KRASG12D; p53R270H cells were cultured in DMEM media. All media contained 10% FBS and 100 IUml$^{-1}$ penicillin/streptomycin. All cells were grown in a humidified incubator at 37° C. with 5% CO2 and were tested regularly for *mycoplasma* contamination. All cell lines used were negative for *mycoplasma*.

Trametinib (S2673), SCH772984 (S7101), Gefitinib (S1025), Crizotinib (S1068), CP-724714 (S1167), Afatinib (S1011), BGJ398 (S2183), AZD4547 (S2801), and Ponatinib (S1490) were obtained from Selleckchem. Drugs for in vitro studies were dissolved in dimethyl sulfoxide (DMSO) to yield 5 or 10 mM stock solutions and stored at −80° C.

For shRNA experiments, human lung cancer cells were modified to express the ecotropic receptor and rtTA3 using retroviral transduction of MSCV-RIEP (MSCV-rtTA3-IRES-EcoR-PGKPuro) followed by drug selection (1 ugml$^{-1}$ puromycin for 1 week). The resulting cell lines were transduced with ecotropically packaged TRMPV-Neo-shRNA retroviruses, selected with 1 mgml$^{-1}$ G418 for 1 week, and treated with 1 µgml$^{-1}$ doxycycline to induce shRNA expression. shRNA-transduced cells were mixed with non-transduced cells (8:2) and cultured with doxycycline in the presence or absence of trametinib (25 nM), and the relative change in Venus+/dsRed+(shRNA expressing) cells was monitored on a Guava Easycyte (Millipore). Experiments were performed independently two or three times.

Lentiviral Production

Lentiviruses were produced by co-transfection of 293T cells with lentiviral-Cre backbone construct and packaging and envelope vectors (psPAX2 and VSV-G) using the calcium phosphate method. Supernatant was collected 48, 60 and 72 h post-transfection, concentrated by ultracentrifugation at 24,000 r.p.m. for 120 min and resuspended in an appropriate volume of HBSS solution (Gibco).

Clonogenic and Apoptosis Assay

For clonogenic assays, cells were seeded in triplicate into 6-well plates (5-10×10$^3$ cells per well) and allowed to adhere overnight in regular growth media. Cells were then cultured in the absence or presence of drug as indicated in complete media for 10-14 days. Growth media with or without drug was replaced every 2 days. Remaining cells were fixed with methanol (1%) and formaldehyde (1%), stained with 0.5% crystal violet, and photographed using a digital scanner. Relative growth was quantified by densitometry after extracting crystal violet from the stained cells using 10% of acetic acid. All experiments were performed at least three times. Representative experiments are shown.

For apoptosis assay, around 1×10$^6$ cells were seeded into 10-cm plates and cultured in the presence or absence of drugs as indicated. After 6 days, apoptosis and cell death were determined using AnnexinV-APC apoptosis detection kit according to the manufacturer's instruction (Affymetrix eBioscience). Data were acquired using a FACS Calibur (BD Biosciences). All experiments were performed independently three times.

Quantitative Analysis of Drug Synergy

Drug synergism was analyzed using CompuSyn software (Version 1.0) (http://www.combosyn.com), which is based on the Median-Effect Principle (Chou) and the Combination Index-Isobologram Theorem (Chou-Talalay). CompuSyn software generates combination index (CI) values, where CI<1 indicates synergism; CI=0.75-1.25 indicates additive effects; and CI>1 indicates antagonism. Following the instruction of the software, drug combinations at non-constant ratios were used to calculate Combination Index (CI) in our study.

Immunoblotting and RAS-GTP Assay.

Phospho-lysis buffer (50 mM Tris pH 7.5, 1% Tween-20, 200 mM NaCl, 0.2% NP-40) supplemented with phosphatase inhibitors (5 mM Sodium Fluoride, 1 mM Sodium Orthovanadate, 1 mM Sodium Pyrophosphate, 1 mM β-glycerophosphate), and protease inhibitors (Protease Inhibitor Cocktail Tablets, Roche) was used for cell lysis and protein concentration was determined by Bradford protein Assay kit (Biorad). Proteins were separated by SDS-Page and immunoblotted and transferred to polyvinyl difluoride (PVDF) membranes (Millipore) according to standard protocols. Membranes were immunoblotted with antibodies against pERK$^{T202/Y204}$ (9101), tERK (9107), pAKT$^{S473}$ (4060), tAKT (9272), pFRS2$^{Y436}$ (3861), pSTAT3$^{Y705}$ (9145), pMEK$^{S217/221}$ (9154), MEK (4694), pMET$^{Y1234/1235}$ (3077), MET (8198), pERBB2$^{Y1221/1222}$ (2243), pEG-FR$^{Y1068}$ (3777), EGFR (4267), pERBB3$^{Y1289}$ (4791), and PTEN (9559) from Cell Signaling; CRAF (SC-227), and BRAF (SC-5284) from Santa Cruz Biotechnology; KRAS (WH0003845M1) from Sigma in 5% BSA in TBS blocking buffer. After primary antibody incubation, membranes were probed with ECL anti-rabbit IgG, anti-mouse IgG or anti-goat IgG secondary antibody (1:10,000) from GE Healthcare Life Science and imaged using the FluorChem M system (protein simple). GTP-bound RAS was measured using the CRAF RAS-binding-domain (RBD) pull down and detection kit (8821, Cell Signaling) as instructed by the manufacturer. All immunoblots were performed independently at least twice.

qRT-PCR

Total RNA was isolated using TRIZOL (Invitrogen), and cDNA was obtained using the TaqMan reverse transcription reagents (Applied Biosystems). Real-time PCR was carried out in triplicate in three independent experiments using SYBR Green PCR Master Mix (Applied Biosystems) on the ViiA™ 7 Real-Time PCR System (Invitrogen). GAPDH or β-actin served as endogenous normalization controls.

Animal Studies

All mouse experiments were approved by the Memorial Sloan Kettering Cancer Center (MSKCC) Animal Care and Use Committee (protocol no. 12-04-006). Mice were maintained under specific pathogen-free conditions, and food and water were provided ad libitum. 5-7-week-old, female athymic NCR-NU-NU (Harlan laboratories) mice were used for animal experiments with human cell lines and patient-derived xenografts. For A549, H23, and H2122 xenografts, cells (10×10$^6$) were harvested on the day of use and injected in growth-factor reduced Matrigel/PBS (50% final concentration). One flank was injected subcutaneously per mouse. For JHU-LX55a patient-derived xenograft, a poorly differentiated lung adenocarcinoma bearing a KRAS$^{G12C}$ mutation, tumors were cut into pieces and inserted into a pocket in the subcutaneous space as previously described. After inoculation, mice were monitored daily, weighed twice weekly, and caliper measurements begun when tumors became visible. Tumor volume was calculated using the following formula: tumor volume=(D×d$^2$)/2, in which D and d refer to the long and short tumor diameter, respectively. When tumors reached a size of 150-300 mm$^3$, mice were randomized into 7-8 per group and treated with vehicle, trametinib and/or ponatinib per os for 5 consecutive days followed by 2 days off treatment, at 3 mg/kg and 30 mg/kg, respectively. No obvious toxicities were observed in the vehicle- or drug-treated animals as assessed by difference in body weight between vehicle- and drug-treated mice taking tumor size into account.

For drug efficacy studies using a genetically engineered mouse model of lung cancer, Kras$^{LSLG12D/+}$ and Trp53$^{fl/fl}$ mice were anaesthetized by intraperitoneal injection of ketamine (80 mg per kg) and xylazine (10 mg per kg) and infected intratracheally with 2.5×10$^5$ infectious particles of Lenti-Cre per mouse, as previously described. Mice were evaluated by µCT imaging to quantify lung tumor burden before being assigned to various treatment study cohorts. Mice were treated with vehicle, trametinib and/or ponatinib per os for 4 consecutive days followed by 3 days off treatment, at 3 mg/kg and 30 mg/kg, respectively. µCT imaging evaluation was repeated every week during the treatment. Investigators were not blind with respect to treatment.

µCT imaging µCT Scans were performed on the Mediso Nano SPECT/CT System covering only the lungfields of each mouse. Each scan averaged approximately 6 min using 240 projections with an exposure time of 1,000 ms set at a pitch of 1 degree. The tube energy of the X-ray was 55 kVp and 145 µA. The in-plane voxel sizes chosen were small and thin creating a voxel size of 73×73×73 µm. The final reconstructed image consisted of 368×368×1,897 voxels. Scans were analysed with the Osirix software.

Patient Samples

Patients with KRAS mutation-positive advanced lung adenocarcinomas were enrolled in the phase I/II clinical study of trametinib and navitoclax (NCT02079740) and the response was assessed per RECIST (response evaluation criteria in solid tumors) criteria. Biopsies were obtained before treatment, and within 2-4 weeks after starting the treatment with trametinib. Specifically, for patient #1, the post-treatment biopsy was obtained after treatment with navitoclax for 7 days, followed by co-treatment with navitoclax and trametinib for 16 days. The post-treatment biopsy from patient #2 was obtained after co-treatment with navitoclax and trametinib for 22 days. All human studies were approved by the Massachusetts General Hospital Institutional Review Board, and informed consent to study was obtained as per protocol from all patients.

Immunohistochemistry

Tissues were fixed overnight in 4% paraformaldehyde, embedded in paraffin, and cut into 5 mm thick sections. Sections were subject to hematoxylin and eosin staining, and immunohistochemical staining following standard protocols. The following primary antibodies were used: $pERK^{T202/Y204}$ (4370) and $pAKT^{S473}$ (4060) (Cell signaling), and $pFRS2^{Y436}$ (ab193363) (Abcam).

Statistical Analysis

Data are expressed as mean±s.e.m or mean±s.d. Group size was determined based on the results of preliminary experiments and no statistical method was used to predetermine sample size. Group allocation and outcome assessment were not performed in a blinded manner. All samples that met proper experimental conditions were included in the analysis. Statistical significance was determined using Student's t-test or two-way ANOVA using Prism 6 software (GraphPad Software). Significance was set at $P<0.05$.

Example 3: Standard Clinical Dosing Regimens

The present Example reports current clinical dosing regimens known in the art for with certain inhibitory agents (e.g., when used as monotherapy) that may be utilized in accordance with the present invention.

Ponatinib: Current recommended clinical dosing regimens for Ponatinib include: (a) a once daily dose of 45 mg *e.g. administered orally (tablet), for the treatment of leukemia with doses of 30 mg or 15 mg in the event of adverse reactions. [Iclusig™ Product Insert]; (b) a once daily dose of 45 mg *e.g. administered orally (tablet), for the treatment of endometrial carcinoma [as reported in NCT01888562] or lung cancer [as reported in NCT01935336]

BGJ398: Current recommended clinical dosing regimens for BGJ398 include: a once daily dose of 125 mg *e.g. administered orally (tablet), for the treatment of solid tumors or hematological malignancies [as reported in NCT02160041].

AZD4547: Current recommended clinical dosing regimens for AZD4547 include: a 2 week on, 1 week off schedule of a once daily dose of 80 mg *e.g administered orally (tablet), for the treatment of breast cancer [as reported in NCT02299999], lung cancer [as reported in NCT01795768], gastric cancer and esophageal cancers [as reported in NCT01457846].

Tramentinib: Current recommended clinical dosing regimens for Ponatinib include: a dose of 2 mg *e.g. administered orally (tablet), for the treatment of unresectable or metastatic melanoma with BRAF mutations [MEKINST™ Product Insert].

EQUIVALENTS

Those skilled in the art will recognize, or be able to ascertain using no more than routine experimentation, many equivalents to the specific embodiments, of the invention described herein. The scope of the present invention is not intended to be limited to the above Description, but rather is as set forth in the following claims:

We claim:

1. A method for treating a subject that (a) suffers from a KRAS mutant lung or pancreatic cancer, and (b) has received or is receiving a small molecule MEK inhibitor comprising:
   administering to the subject a therapeutically effective amount of a FGFR1 inhibitor, wherein the therapeutically effective amount of the FGFR1 inhibitor is sufficient to significantly reduce lung or pancreatic tumor volume compared to a control subject that is suffering from the KRAS mutant lung or pancreatic cancer and has been treated with the small molecule MEK inhibitor, and wherein the FGFR1 inhibitor is or comprises an antibody agent or a small molecule.

2. The method of claim 1, wherein the subject shows resistance to the small molecule MEK inhibitor.

3. The method of claim 1, wherein the subject does not show resistance to the small molecule MEK inhibitor.

4. The method of claim 1, wherein the subject has tumors with detectable FRS2 phosphorylation.

5. The method of claim 1, wherein the small molecule MEK inhibitor is Trametinib.

6. The method of claim 1, wherein the FGFR1 inhibitor is selected from the group consisting of Ponatinib, BGJ398 and AZD4547.

7. The method of claim 1, wherein at least one of the small molecule MEK inhibitor and FGFR1 inhibitor is administered at a reduced dose relative to monotherapy with the small molecule MEK inhibitor or FGFR1 inhibitor.

8. A method of selecting subjects for treatment with a FGFR1 inhibitor comprising:
   (a) detecting elevated FGFR1 levels or activity in tumor samples obtained from subjects suffering from a KRAS mutant lung or pancreatic cancer relative to that observed in a reference sample, wherein the subjects have received a small molecule MEK inhibitor; and
   (b) administering to the subjects that express elevated FGFR1 levels or activity a therapeutically effective amount of a FGFR1 inhibitor, wherein the therapeutically effective amount of the FGFR1 inhibitor is sufficient to significantly reduce lung or pancreatic tumor volume compared to a control subject that is suffering from the KRAS mutant lung or pancreatic cancer and has been treated with the small molecule MEK inhibitor, and wherein the FGFR1 inhibitor is or comprises an antibody agent or a small molecule.

9. The method of claim 8, wherein detecting FGFR1 levels comprises detecting FGFR1 levels on a cell surface; or detecting FGFR1 mRNA levels.

10. A method for treating a subject suffering from a KRAS mutant lung or pancreatic cancer comprising the steps of detecting an increase in FRS2 phosphorylation state in a tumor sample obtained from a subject receiving a small molecule MEK inhibitor relative to that observed in a reference sample; and administering to the subject a therapeutically effective amount of a FGFR1 inhibitor, wherein the therapeutically effective amount of the FGFR1 inhibitor is sufficient to significantly reduce lung or pancreatic tumor volume compared to a control subject that is suffering from the KRAS mutant lung or pancreatic cancer and has been treated with the small molecule MEK inhibitor, and wherein the FGFR1 inhibitor is or comprises an antibody agent or a small molecule.

* * * * *